US012667398B2

(12) United States Patent
Laird, Jr. et al.

(10) Patent No.: US 12,667,398 B2
(45) Date of Patent: *Jun. 30, 2026

(54) DISTAL TIBIAL PLATING SYSTEM

(71) Applicant: GLOBUS MEDICAL, INC., Audubon, PA (US)

(72) Inventors: David Laird, Jr., Birdsboro, PA (US); Alex Bada, Phoenixville, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/830,645

(22) Filed: Sep. 11, 2024

(65) Prior Publication Data

US 2025/0000558 A1     Jan. 2, 2025

Related U.S. Application Data

(63) Continuation of application No. 18/480,055, filed on Oct. 3, 2023, now Pat. No. 12,102,363, which is a continuation of application No. 17/358,538, filed on Jun. 25, 2021, now Pat. No. 11,771,480, which is a continuation of application No. 16/271,227, filed on Feb. 8, 2019, now Pat. No. 11,071,570, which is a continuation-in-part of application No. 15/910,041, filed on Mar. 2, 2018, now Pat. No. 11,224,468.

(51) Int. Cl.
*A61B 17/80* (2006.01)

(52) U.S. Cl.
CPC ...... *A61B 17/8061* (2013.01); *A61B 17/8014* (2013.01); *A61B 17/8057* (2013.01)

(58) Field of Classification Search
CPC ................ A61B 17/80; A61B 17/8004; A61B 17/8014; A61B 17/8052; A61B 17/8057; A61B 17/8061
See application file for complete search history.

(56) References Cited

U.S. PATENT DOCUMENTS

| | | | |
|---|---|---|---|
| 1,105,105 | A | 7/1914 | Sherman |
| 2,486,303 | A | 10/1949 | Longfellow |
| 3,463,148 | A | 8/1969 | Treace |
| 3,510,923 | A | 5/1970 | Blake |
| 3,695,259 | A | 10/1972 | Yost |
| 3,716,050 | A | 2/1973 | Johnston |

(Continued)

FOREIGN PATENT DOCUMENTS

| | | |
|---|---|---|
| CN | 201987653 U | 9/2011 |
| CN | 202313691 U | 7/2012 |

(Continued)

*Primary Examiner* — Eric S Gibson

(57) ABSTRACT

Systems for treating bone fractures are disclosed. Exemplary systems may include a backpack and one or more bone plates for engaging bone members. The backpack may be configured to be temporarily attached to the bone plate in order to provide trajectories for fasteners received by the bone plate. The bone plates can receive one or more screws to secure the bone plates to an underlying bone member. The one or more screws can be inserted into bone plate holes that can be considered locking or non-locking. The bone plates described herein can have particular combinations of locking and/or non-locking holes. Additional bone plate holes can be used to accept sutures, K-wire, or other instrumentation.

8 Claims, 25 Drawing Sheets

(56) References Cited

U.S. PATENT DOCUMENTS

| | | | |
|---|---|---|---|
| 4,219,015 A | 8/1980 | Steinemann |
| 4,493,317 A | 1/1985 | Klaue |
| 4,524,765 A | 6/1985 | de Zbikowski |
| 4,651,724 A | 3/1987 | Berentey et al. |
| 4,683,878 A | 8/1987 | Carter |
| 4,781,183 A | 11/1988 | Casey et al. |
| 4,867,144 A | 9/1989 | Karas et al. |
| 4,896,661 A | 1/1990 | Bogert et al. |
| 4,923,471 A | 5/1990 | Morgan |
| 4,966,599 A | 10/1990 | Pollock |
| 5,002,544 A | 3/1991 | Klaue et al. |
| 5,041,114 A | 8/1991 | Chapman et al. |
| 5,151,103 A | 9/1992 | Tepic et al. |
| 5,259,398 A | 11/1993 | Vrespa |
| 5,364,399 A | 11/1994 | Lowery et al. |
| 5,372,598 A | 12/1994 | Luhr et al. |
| 5,423,826 A | 6/1995 | Coates et al. |
| 5,468,242 A | 11/1995 | Reisberg |
| D365,634 S | 12/1995 | Morgan |
| 5,489,305 A | 2/1996 | Morgan |
| 5,527,311 A | 6/1996 | Procter et al. |
| 5,578,036 A | 11/1996 | Stone et al. |
| 5,601,553 A | 2/1997 | Trebing et al. |
| 5,676,667 A | 10/1997 | Hausman |
| 5,690,631 A | 11/1997 | Duncan et al. |
| 5,709,686 A | 1/1998 | Talos et al. |
| 5,709,687 A | 1/1998 | Pennig |
| 5,718,704 A | 2/1998 | Medoff |
| 5,718,705 A | 2/1998 | Sammarco |
| 5,746,742 A | 5/1998 | Runciman et al. |
| 5,766,175 A | 6/1998 | Martinotti |
| 5,766,176 A | 6/1998 | Duncan |
| 5,779,706 A | 7/1998 | Tschakaloff |
| 5,785,712 A | 7/1998 | Runciman et al. |
| 5,797,914 A | 8/1998 | Leibinger |
| 5,814,048 A | 9/1998 | Morgan |
| 5,925,048 A | 7/1999 | Ahmad et al. |
| 5,938,664 A | 8/1999 | Winquist et al. |
| 5,961,519 A | 10/1999 | Bruce et al. |
| 5,980,540 A | 11/1999 | Bruce |
| 6,001,099 A | 12/1999 | Huebner |
| 6,071,291 A | 6/2000 | Forst et al. |
| 6,093,201 A | 7/2000 | Cooper et al. |
| 6,096,040 A | 8/2000 | Esser |
| 6,107,718 A | 8/2000 | Schustek et al. |
| 6,152,927 A | 11/2000 | Farris et al. |
| 6,206,881 B1 | 3/2001 | Frigg et al. |
| 6,283,969 B1 | 9/2001 | Grusin et al. |
| 6,309,393 B1 | 10/2001 | Tepic et al. |
| 6,322,562 B1 | 11/2001 | Wolter |
| 6,364,882 B1 | 4/2002 | Orbay |
| D458,683 S | 6/2002 | Bryant et al. |
| D458,684 S | 6/2002 | Bryant et al. |
| 6,533,786 B1 | 3/2003 | Needham et al. |
| D479,331 S | 9/2003 | Pike et al. |
| 6,623,486 B1 | 9/2003 | Weaver et al. |
| 6,669,700 B1 | 12/2003 | Farris et al. |
| 6,669,701 B2 | 12/2003 | Steiner et al. |
| 6,712,820 B2 | 3/2004 | Orbay |
| 6,719,759 B2 | 4/2004 | Wagner et al. |
| 6,730,091 B1 | 5/2004 | Pfefferle et al. |
| 6,866,665 B2 | 3/2005 | Orbay |
| 6,955,677 B2 | 10/2005 | Dahners |
| 6,974,461 B1 | 12/2005 | Wolter |
| 7,001,387 B2 | 2/2006 | Farris et al. |
| 7,063,701 B2 | 6/2006 | Michelson |
| 7,090,676 B2 | 8/2006 | Huebner et al. |
| 7,128,744 B2 | 10/2006 | Weaver et al. |
| 7,137,987 B2 | 11/2006 | Patterson et al. |
| 7,153,309 B2 | 12/2006 | Huebner et al. |
| 7,179,260 B2 | 2/2007 | Gerlach et al. |
| 7,250,053 B2 | 7/2007 | Orbay |
| 7,294,130 B2 | 11/2007 | Orbay |
| 7,322,983 B2 | 1/2008 | Harris |
| 7,341,589 B2 | 3/2008 | Weaver et al. |

| | | | |
|---|---|---|---|
| 7,344,538 B2 | 3/2008 | Myerson et al. |
| 7,354,441 B2 | 4/2008 | Frigg |
| 7,604,657 B2 | 10/2009 | Orbay et al. |
| 7,632,277 B2 | 12/2009 | Woll et al. |
| 7,635,381 B2 | 12/2009 | Orbay |
| 7,637,928 B2 | 12/2009 | Fernandez |
| 7,648,508 B2 * | 1/2010 | Lutz ................... A61B 17/842 |
| | | | 606/86 R |
| 7,655,029 B2 | 2/2010 | Niedernberger et al. |
| 7,655,047 B2 | 2/2010 | Swords |
| 7,695,472 B2 | 4/2010 | Young |
| 7,717,946 B2 | 5/2010 | Oepen et al. |
| 7,722,653 B2 | 5/2010 | Young et al. |
| 7,740,648 B2 | 6/2010 | Young et al. |
| D622,853 S | 8/2010 | Raven, III |
| 7,771,457 B2 | 8/2010 | Kay et al. |
| 7,776,076 B2 | 8/2010 | Grady, Jr. et al. |
| 7,857,838 B2 | 12/2010 | Orbay |
| 7,867,260 B2 | 1/2011 | Meyer et al. |
| 7,867,261 B2 | 1/2011 | Sixto, Jr. et al. |
| 7,875,062 B2 | 1/2011 | Lindemann et al. |
| 7,905,910 B2 | 3/2011 | Gerlach et al. |
| 7,909,858 B2 | 3/2011 | Gerlach et al. |
| 7,951,178 B2 | 5/2011 | Jensen |
| 7,951,179 B2 | 5/2011 | Matityahu |
| 7,976,570 B2 | 7/2011 | Wagner et al. |
| D643,121 S | 8/2011 | Millford et al. |
| D646,785 S | 10/2011 | Milford |
| 8,043,297 B2 | 10/2011 | Grady, Jr. et al. |
| 8,057,520 B2 | 11/2011 | Ducharme et al. |
| 8,062,296 B2 | 11/2011 | Orbay et al. |
| 8,100,953 B2 | 1/2012 | White et al. |
| 8,105,367 B2 | 1/2012 | Austin et al. |
| 8,114,081 B2 | 2/2012 | Kohut et al. |
| 8,118,846 B2 | 2/2012 | Leither et al. |
| 8,118,848 B2 | 2/2012 | Ducharme et al. |
| 8,162,950 B2 | 4/2012 | Digeser et al. |
| 8,167,918 B2 | 5/2012 | Strnad et al. |
| 8,177,820 B2 | 5/2012 | Anapliotis et al. |
| 8,246,661 B2 | 8/2012 | Beutter et al. |
| 8,252,032 B2 | 8/2012 | White et al. |
| 8,257,403 B2 | 9/2012 | Den Hartog et al. |
| 8,257,405 B2 | 9/2012 | Haidukewych et al. |
| 8,257,406 B2 | 9/2012 | Kay et al. |
| 8,262,707 B2 | 9/2012 | Huebner et al. |
| 8,267,972 B1 | 9/2012 | Gehlert |
| 8,317,842 B2 | 11/2012 | Graham et al. |
| 8,323,321 B2 | 12/2012 | Gradl |
| 8,337,535 B2 | 12/2012 | White et al. |
| 8,343,155 B2 | 1/2013 | Fisher et al. |
| 8,382,807 B2 | 2/2013 | Austin et al. |
| 8,394,098 B2 | 3/2013 | Orbay et al. |
| 8,394,130 B2 | 3/2013 | Orbay et al. |
| 8,398,685 B2 | 3/2013 | McGarity et al. |
| 8,403,966 B2 | 3/2013 | Ralph et al. |
| 8,419,775 B2 | 4/2013 | Orbay et al. |
| 8,435,272 B2 | 5/2013 | Dougherty et al. |
| 8,439,918 B2 | 5/2013 | Gelfand |
| 8,444,679 B2 | 5/2013 | Ralph et al. |
| 8,491,593 B2 | 7/2013 | Prien et al. |
| 8,506,608 B2 | 8/2013 | Cerynik et al. |
| 8,512,384 B2 | 8/2013 | Beutter et al. |
| 8,512,385 B2 | 8/2013 | White et al. |
| 8,518,090 B2 | 8/2013 | Huebner et al. |
| 8,523,862 B2 | 9/2013 | Murashko, Jr. |
| 8,523,919 B2 | 9/2013 | Huebner et al. |
| 8,523,921 B2 | 9/2013 | Horan et al. |
| 8,540,755 B2 | 9/2013 | Whitmore |
| 8,551,095 B2 | 10/2013 | Fritzinger et al. |
| 8,551,143 B2 | 10/2013 | Norris et al. |
| 8,568,462 B2 | 10/2013 | Sixto, Jr. et al. |
| 8,574,268 B2 | 11/2013 | Chan et al. |
| 8,597,334 B2 | 12/2013 | Mocanu |
| 8,603,147 B2 | 12/2013 | Sixto, Jr. et al. |
| 8,617,224 B2 | 12/2013 | Kozak et al. |
| 8,632,574 B2 | 1/2014 | Kortenbach et al. |
| 8,641,741 B2 * | 2/2014 | Murashko, Jr. ........ A61B 17/88 |
| | | | 606/280 |
| 8,641,744 B2 | 2/2014 | Weaver et al. |

(56) References Cited

U.S. PATENT DOCUMENTS

| | | | |
|---|---|---|---|
| 8,663,224 B2 | 3/2014 | Overes et al. | |
| 8,728,082 B2 | 5/2014 | Fritzinger et al. | |
| 8,728,126 B2 | 5/2014 | Steffen | |
| 8,740,905 B2 * | 6/2014 | Price | A61B 17/8861 |
| | | | 606/71 |
| 8,747,442 B2 | 6/2014 | Orbay et al. | |
| 8,764,751 B2 | 7/2014 | Orbay et al. | |
| 8,764,808 B2 | 7/2014 | Gonzalez-Hernandez | |
| 8,777,998 B2 * | 7/2014 | Daniels | A61B 17/8057 |
| | | | 606/291 |
| 8,790,376 B2 | 7/2014 | Fritzinger et al. | |
| 8,790,377 B2 | 7/2014 | Ralph et al. | |
| 8,808,333 B2 | 8/2014 | Kuster et al. | |
| 8,808,334 B2 | 8/2014 | Strnad et al. | |
| 8,834,532 B2 | 9/2014 | Velikov et al. | |
| 8,834,537 B2 | 9/2014 | Castanada et al. | |
| 8,852,246 B2 | 10/2014 | Hansson | |
| 8,852,249 B2 | 10/2014 | Ahrens et al. | |
| 8,864,802 B2 * | 10/2014 | Schwager | A61B 17/8057 |
| | | | 606/286 |
| 8,870,931 B2 | 10/2014 | Dahners et al. | |
| 8,888,825 B2 | 11/2014 | Batsch et al. | |
| 8,906,076 B2 | 12/2014 | Mocanu et al. | |
| 8,911,482 B2 | 12/2014 | Lee et al. | |
| 8,926,675 B2 | 1/2015 | Leung et al. | |
| 8,940,026 B2 | 1/2015 | Hilse et al. | |
| 8,940,028 B2 | 1/2015 | Austin et al. | |
| 8,940,029 B2 | 1/2015 | Leung et al. | |
| 8,951,291 B2 | 2/2015 | Impellizzeri | |
| 8,968,368 B2 * | 3/2015 | Tepic | A61B 17/80 |
| | | | 606/280 |
| 8,979,866 B2 | 3/2015 | Patel et al. | |
| 9,011,457 B2 * | 4/2015 | Grady, Jr. | A61B 17/1728 |
| | | | 606/96 |
| 9,023,052 B2 | 5/2015 | Lietz et al. | |
| 9,050,151 B2 * | 6/2015 | Schilter | A61B 17/1728 |
| 9,072,555 B2 | 7/2015 | Michel | |
| 9,072,557 B2 | 7/2015 | Fierlbeck et al. | |
| 9,107,678 B2 | 8/2015 | Murner et al. | |
| 9,107,711 B2 | 8/2015 | Hainard | |
| 9,107,713 B2 | 8/2015 | Horan et al. | |
| 9,107,718 B2 * | 8/2015 | Isch | A61B 17/80 |
| 9,113,970 B2 | 8/2015 | Lewis et al. | |
| 9,149,310 B2 | 10/2015 | Fritzinger et al. | |
| 9,161,791 B2 | 10/2015 | Frigg | |
| 9,161,795 B2 | 10/2015 | Chasbrummel et al. | |
| 9,168,075 B2 | 10/2015 | Dell'Oca | |
| 9,179,950 B2 | 11/2015 | Zajac et al. | |
| 9,179,956 B2 | 11/2015 | Cerynik et al. | |
| 9,180,020 B2 | 11/2015 | Gause et al. | |
| 9,211,151 B2 * | 12/2015 | Weaver | A61B 17/8061 |
| 9,259,217 B2 | 2/2016 | Fritzinger et al. | |
| 9,259,255 B2 | 2/2016 | Lewis et al. | |
| 9,271,769 B2 | 3/2016 | Batsch et al. | |
| 9,283,010 B2 | 3/2016 | Medoff et al. | |
| 9,295,506 B2 * | 3/2016 | Raven, III | A61B 17/809 |
| 9,314,284 B2 | 4/2016 | Chan et al. | |
| 9,320,554 B2 | 4/2016 | Greenberg et al. | |
| 9,322,562 B2 | 4/2016 | Takayama et al. | |
| 9,370,388 B2 * | 6/2016 | Globerman | A61B 17/8685 |
| D765,851 S | 9/2016 | Early et al. | |
| 9,433,407 B2 | 9/2016 | Fritzinger et al. | |
| 9,433,452 B2 | 9/2016 | Weiner et al. | |
| 9,468,479 B2 | 10/2016 | Marotta et al. | |
| 9,480,512 B2 | 11/2016 | Orbay | |
| 9,486,262 B2 * | 11/2016 | Andermahr | A61B 17/809 |
| 9,492,213 B2 | 11/2016 | Orbay | |
| 9,510,878 B2 | 12/2016 | Nanavati et al. | |
| 9,510,880 B2 | 12/2016 | Terrill et al. | |
| 9,526,543 B2 | 12/2016 | Castaneda et al. | |
| 9,545,277 B2 * | 1/2017 | Wolf | A61B 17/8057 |
| 9,549,819 B1 | 1/2017 | Bravo et al. | |
| 9,566,097 B2 | 2/2017 | Fierlbeck et al. | |
| 9,579,133 B2 | 2/2017 | Guthlein | |
| 9,622,799 B2 | 4/2017 | Orbay et al. | |
| 9,636,157 B2 | 5/2017 | Medoff | |
| 9,649,141 B2 | 5/2017 | Raven, III et al. | |
| 9,668,794 B2 | 6/2017 | Kuster et al. | |
| 9,801,670 B2 | 10/2017 | Hashmi et al. | |
| 9,814,504 B2 | 11/2017 | Ducharme et al. | |
| 10,368,928 B2 * | 8/2019 | Lueth | A61B 17/1728 |
| 10,383,668 B2 * | 8/2019 | Rutledge | A61B 17/8014 |
| 10,420,596 B2 * | 9/2019 | Davison | A61B 17/8014 |
| 10,631,903 B2 * | 4/2020 | Govey | A61B 17/8085 |
| 10,687,873 B2 * | 6/2020 | Langdale | A61B 17/8061 |
| 10,856,920 B2 * | 12/2020 | Tiongson | A61B 17/8061 |
| 11,071,570 B2 * | 7/2021 | Laird, Jr. | A61B 17/8061 |
| 11,224,468 B2 * | 1/2022 | Laird, Jr. | A61B 17/848 |
| 11,771,480 B2 * | 10/2023 | Laird, Jr. | A61B 17/8085 |
| | | | 606/70 |
| 12,102,363 B2 * | 10/2024 | Laird, Jr. | A61B 17/8057 |
| 12,343,051 B2 * | 7/2025 | Laird, Jr. | A61B 17/8014 |
| 2002/0045901 A1 | 4/2002 | Wagner et al. | |
| 2004/0097937 A1 | 5/2004 | Pike et al. | |
| 2005/0107796 A1 | 5/2005 | Gerlach et al. | |
| 2005/0131413 A1 | 6/2005 | O'Driscoll et al. | |
| 2005/0187551 A1 | 8/2005 | Orbay et al. | |
| 2006/0116679 A1 * | 6/2006 | Lutz | A61B 17/80 |
| | | | 606/281 |
| 2006/0149265 A1 | 7/2006 | James et al. | |
| 2006/0173458 A1 * | 8/2006 | Forstein | A61B 17/1728 |
| | | | 606/281 |
| 2006/0229618 A1 * | 10/2006 | Dube | A61B 17/8042 |
| | | | 606/295 |
| 2006/0241607 A1 | 10/2006 | Myerson et al. | |
| 2007/0173840 A1 | 7/2007 | Huebner | |
| 2007/0270849 A1 | 11/2007 | Orbay et al. | |
| 2007/0288022 A1 | 12/2007 | Lutz | |
| 2008/0021477 A1 | 1/2008 | Strnad et al. | |
| 2008/0234749 A1 | 9/2008 | Forstein | |
| 2008/0275510 A1 | 11/2008 | Schonhardt et al. | |
| 2009/0024172 A1 | 1/2009 | Pizzicara | |
| 2009/0024173 A1 | 1/2009 | Reis, Jr. | |
| 2009/0118773 A1 | 5/2009 | James et al. | |
| 2009/0143825 A1 * | 6/2009 | Graham | A61B 17/8061 |
| | | | 606/280 |
| 2009/0157086 A1 * | 6/2009 | Digeser | A61B 17/1728 |
| | | | 606/280 |
| 2009/0198285 A1 | 8/2009 | Raven, III | |
| 2009/0228010 A1 | 9/2009 | Gonzalez-Hernandez et al. | |
| 2009/0228047 A1 | 9/2009 | Derouet et al. | |
| 2009/0248084 A1 | 10/2009 | Hintermann | |
| 2009/0281543 A1 | 11/2009 | Orbay et al. | |
| 2009/0299369 A1 | 12/2009 | Orbay et al. | |
| 2009/0312760 A1 | 12/2009 | Forstein et al. | |
| 2010/0030277 A1 * | 2/2010 | Haidukewych | A61B 17/8061 |
| | | | 606/301 |
| 2010/0057086 A1 | 3/2010 | Price et al. | |
| 2010/0114097 A1 | 5/2010 | Siravo et al. | |
| 2010/0121326 A1 | 5/2010 | Woll et al. | |
| 2010/0179599 A1 * | 7/2010 | Derouet | A61B 17/1735 |
| | | | 606/301 |
| 2010/0274247 A1 | 10/2010 | Grady, Jr. et al. | |
| 2011/0106086 A1 * | 5/2011 | Laird | A61B 17/1728 |
| | | | 606/70 |
| 2011/0218580 A1 | 9/2011 | Schwager et al. | |
| 2011/0313422 A1 * | 12/2011 | Schwager | A61B 17/8057 |
| | | | 606/71 |
| 2012/0010667 A1 | 1/2012 | Eglseder | |
| 2012/0059424 A1 | 3/2012 | Epperly et al. | |
| 2012/0078312 A1 * | 3/2012 | Federspiel | A61B 17/808 |
| | | | 606/281 |
| 2012/0197303 A1 * | 8/2012 | King | A61B 17/1728 |
| | | | 606/282 |
| 2012/0203227 A1 | 8/2012 | Martin | |
| 2012/0232599 A1 | 9/2012 | Schoenly et al. | |
| 2012/0253347 A1 * | 10/2012 | Murashko, Jr. | A61B 17/1782 |
| | | | 606/71 |
| 2012/0323284 A1 | 12/2012 | Baker et al. | |
| 2013/0018426 A1 | 1/2013 | Tsai et al. | |
| 2013/0046347 A1 | 2/2013 | Cheng et al. | |
| 2013/0060291 A1 | 3/2013 | Petersheim | |

(56)  References Cited

U.S. PATENT DOCUMENTS

| | | | |
|---|---|---|---|
| 2013/0123841 A1 | 5/2013 | Lyon | |
| 2013/0138156 A1 | 5/2013 | Derouet | |
| 2013/0150902 A1 | 6/2013 | Leite | |
| 2013/0165981 A1 | 6/2013 | Clasbrummet et al. | |
| 2013/0211463 A1 | 8/2013 | Mizuno et al. | |
| 2013/0238032 A1* | 9/2013 | Schilter | A61B 17/846 |
| | | | 606/281 |
| 2013/0289630 A1 | 10/2013 | Fritzinger | |
| 2014/0005728 A1 | 1/2014 | Koay et al. | |
| 2014/0018862 A1 | 1/2014 | Koay et al. | |
| 2014/0031879 A1 | 1/2014 | Sixto, Jr. et al. | |
| 2014/0066998 A1 | 3/2014 | Martin | |
| 2014/0094856 A1 | 4/2014 | Sinha | |
| 2014/0121710 A1 | 5/2014 | Weaver et al. | |
| 2014/0180345 A1 | 6/2014 | Chan et al. | |
| 2014/0277178 A1 | 9/2014 | O'Kane et al. | |
| 2014/0277181 A1 | 9/2014 | Garlock | |
| 2014/0316473 A1 | 10/2014 | Pfeffer et al. | |
| 2014/0330320 A1 | 11/2014 | Wolter | |
| 2014/0378975 A1 | 12/2014 | Castaneda et al. | |
| 2015/0051650 A1 | 2/2015 | Verstreken et al. | |
| 2015/0051651 A1 | 2/2015 | Terrill et al. | |
| 2015/0073486 A1 | 3/2015 | Marotta et al. | |
| 2015/0105829 A1 | 4/2015 | Laird | |
| 2015/0112355 A1 | 4/2015 | Dahners et al. | |
| 2015/0134011 A1 | 5/2015 | Medoff | |
| 2015/0142065 A1 | 5/2015 | Schonhardt et al. | |
| 2015/0190185 A1 | 7/2015 | Koay et al. | |
| 2015/0209091 A1 | 7/2015 | Sixto, Jr. et al. | |
| 2015/0216571 A1 | 8/2015 | Impellizzeri | |
| 2015/0223852 A1 | 8/2015 | Lietz et al. | |
| 2015/0272638 A1 | 10/2015 | Langford | |
| 2015/0282851 A1 | 10/2015 | Michel | |
| 2015/0313653 A1 | 11/2015 | Ponce et al. | |
| 2015/0313654 A1 | 11/2015 | Horan et al. | |
| 2015/0327898 A1 | 11/2015 | Martin | |
| 2015/0351816 A1 | 12/2015 | Lewis et al. | |
| 2015/0374421 A1 | 12/2015 | Rocci et al. | |
| 2016/0022336 A1 | 1/2016 | Bateman | |
| 2016/0030035 A1 | 2/2016 | Zajac et al. | |
| 2016/0031018 A1 | 2/2016 | Ota et al. | |
| 2016/0045237 A1 | 2/2016 | Cerynik et al. | |
| 2016/0045238 A1 | 2/2016 | Bohay et al. | |
| 2016/0074081 A1 | 3/2016 | Weaver et al. | |
| 2016/0166297 A1 | 6/2016 | Mighell et al. | |
| 2016/0166298 A1 | 6/2016 | Mighell et al. | |
| 2016/0183990 A1 | 6/2016 | Koizumi et al. | |
| 2016/0262814 A1 | 9/2016 | Wainscott | |
| 2016/0278828 A1 | 9/2016 | Ragghianti | |
| 2016/0310183 A1 | 10/2016 | Shah et al. | |
| 2016/0310185 A1 | 10/2016 | Sixto et al. | |
| 2016/0324552 A1 | 11/2016 | Baker et al. | |
| 2016/0354122 A1 | 12/2016 | Montello et al. | |
| 2017/0035478 A1 | 2/2017 | Andermahr et al. | |
| 2017/0042592 A1 | 2/2017 | Kim | |
| 2017/0042596 A9 | 2/2017 | Mighell et al. | |
| 2017/0049493 A1* | 2/2017 | Gauneau | A61B 17/808 |
| 2017/0065312 A1 | 3/2017 | Lauf et al. | |
| 2017/0105775 A1 | 4/2017 | Ricker et al. | |
| 2017/0215931 A1 | 8/2017 | Cremer et al. | |
| 2017/0296248 A1 | 10/2017 | Paulisch et al. | |
| 2018/0049784 A1* | 2/2018 | Gault | A61B 17/8014 |
| 2018/0256223 A1* | 9/2018 | Lueth | A61B 17/809 |
| 2019/0076175 A1* | 3/2019 | Tiongson | A61B 17/8057 |
| 2019/0269443 A1* | 9/2019 | Laird, Jr. | A61B 17/848 |
| 2019/0269446 A1* | 9/2019 | Laird, Jr. | A61B 17/8061 |
| 2021/0315615 A1* | 10/2021 | Laird, Jr. | A61B 17/8057 |
| 2022/0110665 A1* | 4/2022 | Laird, Jr. | A61B 17/8061 |
| 2024/0024003 A1* | 1/2024 | Laird, Jr. | A61B 17/8014 |
| 2025/0000558 A1* | 1/2025 | Laird, Jr. | A61B 17/8014 |

FOREIGN PATENT DOCUMENTS

| | | | | |
|---|---|---|---|---|
| CN | 202821574 U | 3/2013 | | |
| CN | 202821575 U | 3/2013 | | |
| CN | 203506858 U | 4/2014 | | |
| CN | 203815563 U | 9/2014 | | |
| CN | 105982727 A | 10/2016 | | |
| CN | 206964672 U | 2/2018 | | |
| EP | 3202348 A1 | 8/2017 | | |
| EP | 3398526 A1 * | 11/2018 | | A61B 17/809 |
| FR | 2846870 A1 | 5/2004 | | |
| FR | 2928259 A1 | 9/2009 | | |
| JP | 2003210478 A | 7/2003 | | |
| JP | 2006150055 A | 6/2006 | | |
| JP | 2007-518537 A | 7/2007 | | |
| JP | 2010259823 A | 11/2010 | | |
| JP | 2014050722 A | 3/2014 | | |
| TW | 201316942 A | 5/2013 | | |
| WO | 2016079504 A1 | 5/2016 | | |
| WO | 2017/035302 A1 | 3/2017 | | |

* cited by examiner

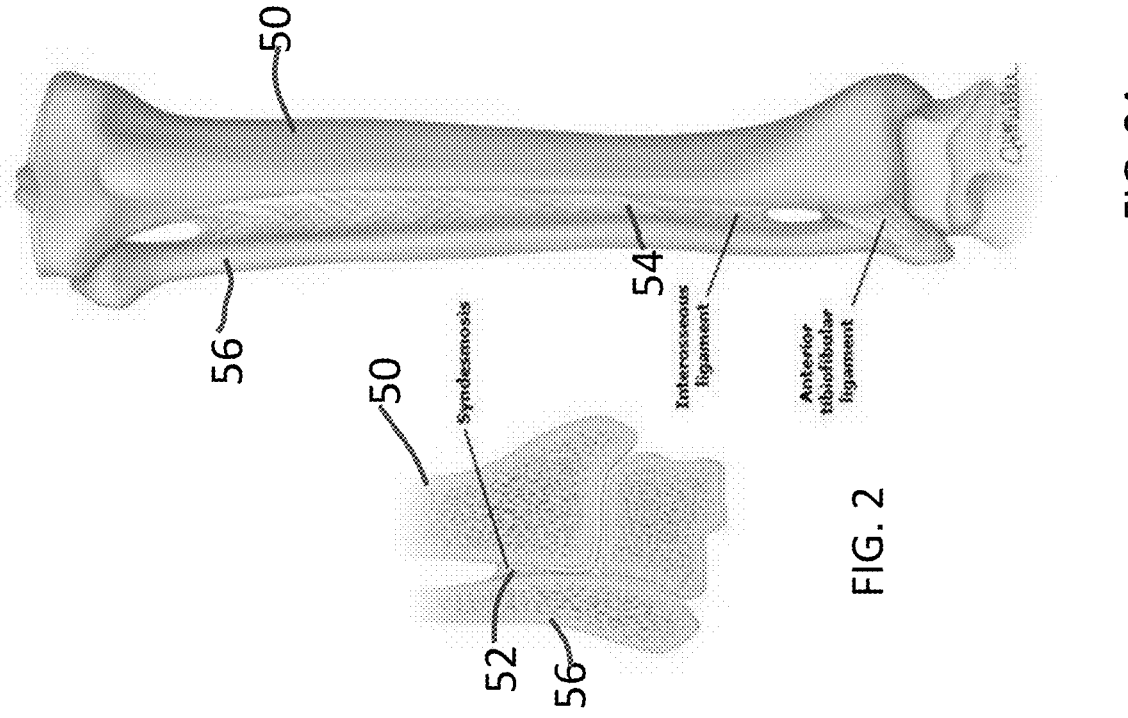
FIG. 2A
FIG. 2
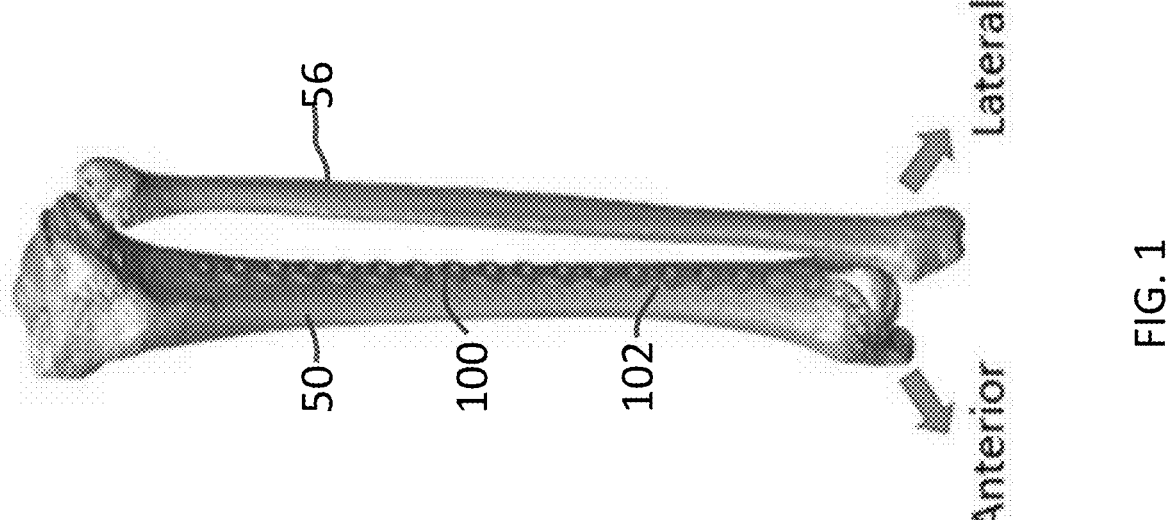
FIG. 1

4104

4102

DISTAL TIBIAL PLATING SYSTEM

CROSS-REFERENCE TO RELATED APPLICATIONS

The present application is a continuation of U.S. patent application Ser. No. 18/480,055 filed on Oct. 3, 2023, which is a continuation of U.S. patent application Ser. No. 17/358, 538 filed on Jun. 25, 2021, which is a continuation of U.S. patent application Ser. No. 16/271,227 filed on Feb. 8, 2019, which is a continuation-in-part of U.S. application Ser. No. 15/910,041 filed on Mar. 2, 2018, all of which are hereby incorporated by reference in their entirety.

FIELD OF THE INVENTION

The present disclosure relates to surgical devices, systems, and methods, and more particularly, stabilization systems including plates, for example, for trauma applications.

BACKGROUND OF THE INVENTION

Bone fractures can be healed using plating systems. During treatment, one or more screws are placed on either side of a fracture, thereby causing compression and healing of the fracture. There is a need for improved plating systems as well as mechanisms for accurate use of the plating systems.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In accordance with the application, a system for treating a fracture in a bone is provided. In some embodiments, the system comprises a backpack and a bone plate configured to engage the bone. The bone plate includes an inferior end having a base portion extending along a first axis. The base portion comprises a first row of holes and a second row of holes for receiving one or more fasteners therein. A superior end has a shaft portion connected to the base portion. The shaft portion extends along a second axis, different from the first axis and comprises at least one additional hole for receiving a fastener therein. At least one fastener is received in the base portion and is positioned in the first row of holes or second row of holes. At least one additional fastener is also received in the shaft portion and is positioned in the at least one additional hole. Further, the backpack may be configured to be temporarily attached to the base portion and configured to provide a trajectory of insertion for the at least one fastener received in the base portion.

In other embodiments, the system comprises a backpack and a bone plate configured to engage the bone. The bone plate comprises an inferior end having a base portion. The base portion has a first type of hole formed therethrough and a second type of hole formed therethrough. A superior end has a shaft portion. The shaft portion has a third type of hole formed therethrough and a fourth type of hole formed therethrough. At least one fastener is received in the base portion and positioned in the first type of hole, wherein the at least one fastener is non-threaded. At least one additional fastener is received in the shaft portion and positioned in the third type of hole. Further, the backpack may be configured to be temporarily attached to the base portion and configured to provide a trajectory of insertion for the at least one fastener received in the base portion.

In still other embodiments, the system comprises a bone plate configured to engage the bone. The bone plate comprises an inferior end having a base portion. The base portion has a first plurality of holes formed therethrough. A superior end has a shaft portion. The shaft portion has a second plurality of holes formed therethrough. The shaft portion also has an undercut contact surface and a plurality of side relief cuts formed therein between adjacent holes of the second plurality of holes. At least one fastener is received in the base portion and is positioned one of the first plurality of holes. At least one additional fastener is received in the shaft portion and positioned in one of the second plurality of holes. Further, the backpack may be configured to be temporarily attached to the base portion and configured to provide a trajectory of insertion for the at least one fastener received in the base portion.

Also provided are stabilization systems, methods for installing the stabilization systems, and kits including bone plates, fasteners, and components and instruments for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 1 is a side elevational view of a bone plate assembly in accordance with some embodiments attached to a tibia.

FIG. 2 is a sectional view of an inferior end of a tibia and fibula.

FIG. 2A perspective view of a tibia and fibula and associated ligaments.

DETAILED DESCRIPTION OF THE INVENTION

Figures 3, 4:
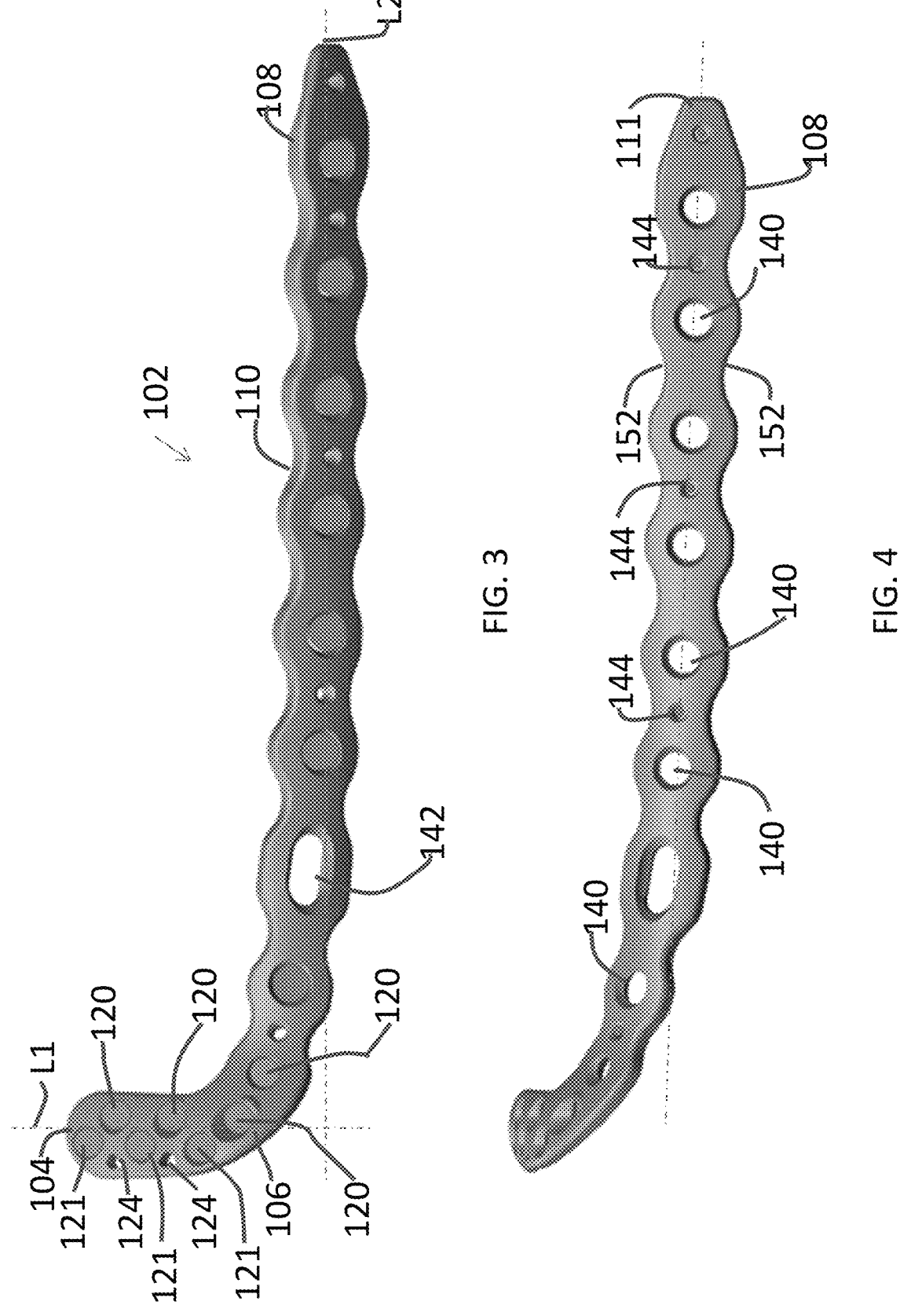
FIG. 3 is a side perspective view of the bone plate of FIG. 1.
FIG. 4 is a front elevational view of the bone plate of FIG. 1.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "superior" is defined as a direction toward an upper portion of a patient and "inferior" is defined as a direction toward a lower portion of the patient.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Embodiments of the present application are generally directed to devices, systems and methods for bone stabilization. In particular, embodiments are directed to bone plates that extend across bone members to treat one or more fractures.

The plates described herein may be adapted to contact one or more bones. For example, the plates may fit one more long bones, such as a femur, a distal tibia, a proximal tibia, a proximal humerus, a distal humerus, a clavicle, a fibula, an ulna, a radius, bones of the foot, bones of the hand, or other suitable bone or bones. The bone plates may be curved, contoured, straight, or flat. The plates may have a base portion that is contoured to match a particular bone surface, such as a metaphysis or diaphysis, flares out from the shaft portion, forms an L-shape, T-shape, Y-shape, etc., with the shaft portion, or that forms any other appropriate shape to fit the anatomy of the bone to be treated. The plates may be adapted to secure small or large bone fragments, single or multiple bone fragments, or otherwise secure one or more fractures. In particular, the systems may include a series of trauma plates and screws designed for the fixation of fractures and fragments in diaphyseal and metaphyseal bone. Different bone plates may be used to treat various types and locations of fractures.

The bone plates can be comprised of titanium, stainless steel, cobalt chrome, carbon composite, plastic or polymer-such as polyetheretherketone (PEEK), polyethylene, ultra high molecular weight polyethylene (UHMWPE), resorbable polylactic acid (PLA), polyglycolic acid (PGA), combinations or alloys of such materials or any other appropriate material that has sufficient strength to be secured to and hold bone, while also having sufficient biocompatibility to be implanted into a body. Similarly, the bone plates may receive one or more screws or fasteners may be comprised of titanium, cobalt chrome, cobalt-chrome-molybdenum, stainless steel, tungsten carbide, combinations or alloys of such materials or other appropriate biocompatible materials. Although the above list of materials includes many typical materials out of which bone plates and fasteners are made, it should be understood that bone plates and fasteners comprised of any appropriate material are contemplated.

Figures 5, 6, 7:
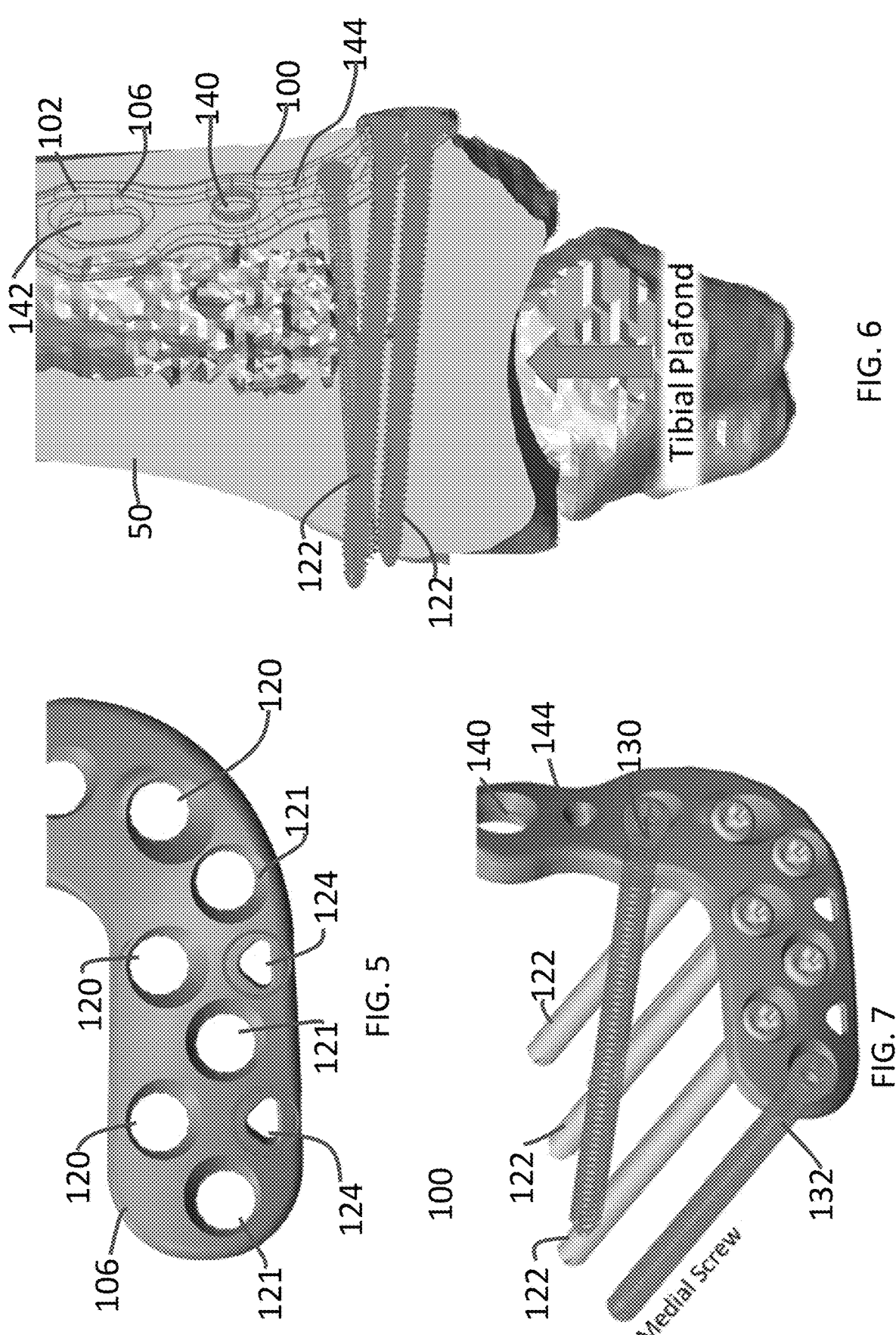
FIG. 5 is an enlarged front elevational view of an inferior end of the bone plate of FIG. 3.
FIG. 6 is a perspective view of the inferior end of the bone plate of FIG. 3 with a plurality of screws inserted therethrough.
FIG. 7 is a sectional view of tibia with the bone plate of FIG. 1 attached thereto.

The bone plates described herein can be considered "locking" or "non-locking" plates. Locking plates include one or more openings for accepting one or more locking fasteners. The one or more openings can be partially or fully threaded. In some embodiments, these openings include fully threaded or stacked openings, which accept both locking and non-locking fasteners. In some embodiments, the locking fasteners include heads that are at least partially threaded. The locking fasteners can be monoaxial or polyaxial. One non-limiting example of a locking fastener (among others) is shown in FIG. 6 of U.S. Ser. No. 15/405,368, filed Jan. 13, 2017, which is hereby incorporated by reference in its entirety for all purposes.

Non-locking plates may include one or more openings for accepting one or more non-locking fasteners. The one or more openings at least in part are non-threaded. In some embodiments, these openings include non-threaded or stacked openings, which accept both locking and non-locking fasteners. In some embodiments, the non-locking fasteners include heads that are non-threaded. The non-locking fasteners can be monoaxial or polyaxial. One non-limiting example of a non-locking fastener (among others) is shown in FIG. 4 of U.S. Ser. No. 15/405,368, filed Jan. 13, 2017, which is hereby incorporated by reference in its entirety for all purposes. In some embodiments, the non-locking fasteners can include dynamic compression screws, which enable dynamic compression of an underlying bone.

Below are various examples of locking and non-locking plates attachable to bone. In some embodiments, locking plates may be thicker than non-locking plates. Locking plates may be useful for patients that have weaker bone, while non-locking plates may be useful for patients that have strong bone.

The locking and non-locking plates described below can be attached to different bones to treat fractures. In particular, the locking and non-locking plates can be used to treat fractures of the tibia, although one skilled in the art will appreciate that the novel plates described herein can be applied to fractures on other types of bone as well. Implants with anatomic shapes suitable for fixation at distinct regions of the tibia include anterolateral plates, medial plates, posterior T-plates, metaphyseal plates, anterior plates, and posterolateral plates. In other words, the plates can be attached to the above recited aspects of a tibia. One skilled in the art will appreciate, however, that the plates are not limited to their specific locations on the tibia, and that a surgeon may choose to, for example, apply a lateral plate distally or a distal plate laterally, if desired, and according to the anatomy of a particular patient.

FIGS. 1 and 3-15 disclose an anterolateral bone plate system 100 ("system 100") in accordance with a first embodiment. Referring to FIGS. 1-2A, system 100 is attached to a tibia 50 and is contoured to fit along the anterior-lateral portion of the tibia 50 along the syndesmosis 52 and the interosseous ligament 54 and extend onto the anterior portion of the tibia 50 (FIG. 1). The syndesmosis is a ligamentous attachment between the fibula 56 and the tibia 50 (See FIGS. 2 and 2A). An anterolateral bone plate 102 of system 100 is specific to the left and right tibia.

Referring to FIGS. 3 and 4, the bone plate 102 has a plurality of through holes formed therein for receiving fasteners, wherein at least some of the fasteners received therein are locking fasteners. The bone plate 102 comprises an inferior end 104 having a base portion 106 and a superior end 108 having a shaft portion 110. The bone plate 102 is multi-planar, with the shaft portion 110 extending generally in a singular plane, while the base portion 106 is curved away from the plane and extends across more than one plane. The curvature of the base portion 106 relative to the shaft portion 110 can be adjusted to match the anatomy of a particular patient.

The base portion 106 extends along a first longitudinal axis L1. In some embodiments, the inferior end 104 is chamfered around its perimeter. Advantageously, the contour and chamfer of the inferior end 104 helps to position the bone plate 102 to minimize soft tissue irritation. In some embodiments, the base portion 106 will be placed on a bone member (e.g., tibia) near an articular surface. Certain features of the base portion 106 are advantageously designed to prevent or resist subsidence of an articular surface.

In an exemplary embodiment, as shown in FIGS. 5 and 6, the base portion 106 features two (2) rows of three (3) 2.5 mm polyaxial screw holes 120, 121. These holes 120, 121 are through holes for receiving rafting screws 122 that are closest to an articular surface of a joint. The purpose of these screws 122 is to capture articular fragments and provide a rafting construct. The nominal screw trajectories are parallel to the tibial plafond (joint surface) and support the articular fragments to maintain their alignment and rotation relative to the shaft of the tibia 50, as shown in FIG. 7.

By providing two sets of holes 120, 121, the bone plate 102 advantageously accommodates a greater number of rafting screws 122, thereby providing greater support near the joint. In some embodiments, the first row of holes 120 are offset from the second row of holes 121, while in other embodiments, the first row of holes 120 are aligned with the second row of holes 121. In some embodiments, the first row of holes 120 can have the same number of holes as the second row of holes 121, while in other embodiments, the first row of holes 120 can have a different number of holes than the second row of holes 121. In the present embodiment, the bone plate 102 includes three (3) holes 120 and three (3) holes 121.

Figures 8, 9:
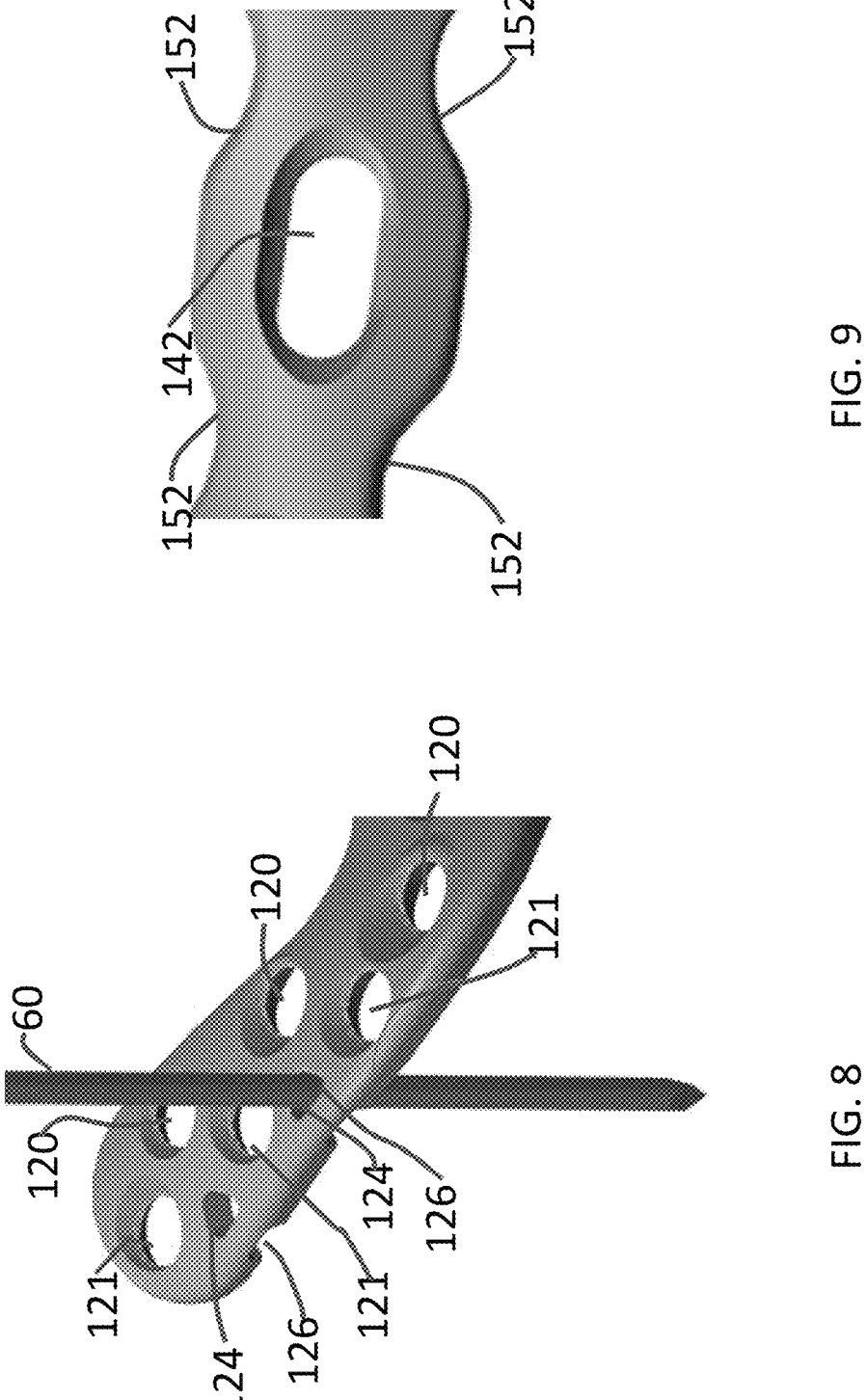
FIG. 8 is a perspective view of the inferior end of the bone plate of FIG. 3 with a K-wire inserted therethrough.
FIG. 9 is an enlarged top plan view of a portion of the superior end of the bone plate of FIG. 1 showing a dynamic compression plating ("DCP") slot.

As shown in FIGS. 3 and 5, the most inferior edge of the base portion 106 further comprises one or more novel multi-purpose holes 124. The multi-purpose holes 124 are smaller than the holes 120, 121. In some embodiments, the multi-purpose holes 124 enable passage of suture/needles to serve as anchor points useful for reattachment and repositioning of soft tissue damaged during surgery. This may aid post-surgical soft tissue healing. The multi-purpose holes 124 also allow for a non-threaded 1.6 mm K-wire 60 to be provisionally placed, as shown in FIG. 8. As shown in FIG. 8, one or more undercuts 126 advantageously allow access to one or more sutures through the bone plate 102 even after the bone plate 102 is implanted on bone. The sutures can be used to attach the bone plate 102 to adjacent tissue, thereby further securing the bone plate 102 at or near a surgical site.

Additionally, referring to FIG. 6, the plate 102 features a single kickstand screw 130 that is angled towards the tip of the most medial screw 132. The purpose of the kickstand screw 130 is to provide additional stability of the articular fragments and aid in axial loading of the tibia 50.

Referring back to FIGS. 3 and 4, the shaft portion 110 is connected to the base portion 106. The shaft portion 110 extends along a second axis L2, different from the first axis L1. A plurality of polyaxial through holes 140 extend along the length of the shaft portion 110 and accept locking and non-locking screws, both inserted within a cone of angulation. At least four (4) holes 140 are provided and are sized to accept 3.5 mm screws.

The most superior portion of the shaft portion 110 further comprises a tapered tip 111. In some embodiments, the tapered tip 111 serves as an insertion tip that allows the plate 102 to be inserted beneath skin to a surgical site. The bone plate 102 can be positioned adjacent to bone (e.g., a tibia), whereby the plate 102 can be fixed to the bone. In some embodiments, the tapered tip 111 allows for simplified submuscular plate insertion to minimize incision length.

Figure 10:
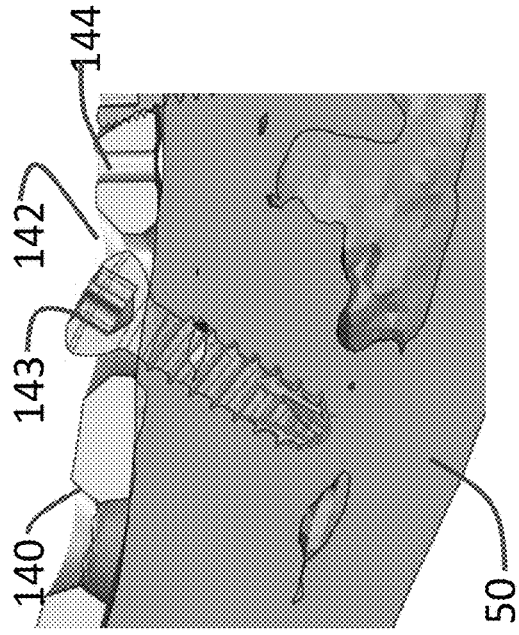
FIG. 10 is a sectional view of a bone with a screw inserted thereinto through the DCP slot of FIG. 9.

As shown in FIGS. 9 and 10, a dynamic compression plating ("DCP") slot 142 allows lateral motion of the plate 102 relative to the bone to compress a bone fracture. 3.5 mm non-locking screws 143 are used for this technique as well as standard neutral placement in the center of the slot 142. The DCP slot 142 is a through hole that also enables off-axis, or oblique, screw trajectories in the plane of the slot using 3.5 mm non-locking screws 143, as shown in FIG. 10. Alternatively, 4.0 mm cancellous screws enable oblique or neutral screw trajectories through the DCP slot 142, which can be useful for fragment capture or load neutralization across the fracture line. In some embodiments, the DCP slot 142 has a length that is greater than a length of any of the other holes 120, 121, 140 that receive bone screws therein. In some embodiments, the DCP slot 142 has a length that is at least twice the length of a length of any of the other holes 120, 121, 140 that receive bone screws therein.

K-wire through holes 144 are placed along the length of the plate 102, typically on either side of a through hole 140, to provide provisional fixation. The holes 144 allow for a 1.6 mm K-wire to be placed provisionally.

Figure 11:
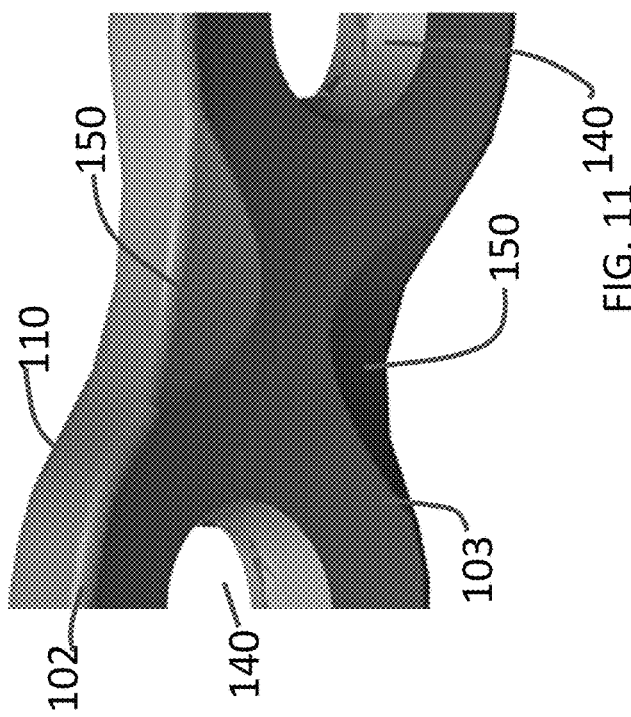
FIG. 11 is an enlarged rear perspective view of a portion of the superior end of the bone plate of FIG. 1.

Referring to FIG. 11, cylindrical undercuts 150 are formed on the rear surface 103 of the plate 102 between adjacent screw holes 140 to help reduce the moment of inertia between adjacent screw holes 140 to allow preferential bending between the holes 140, thereby helping to minimize deformation of the screw holes 140. This feature is useful for contour customization of the plate 102. In some embodiments, the undercuts 150 minimize impact to the periosteal blood supply.

Figure 12:
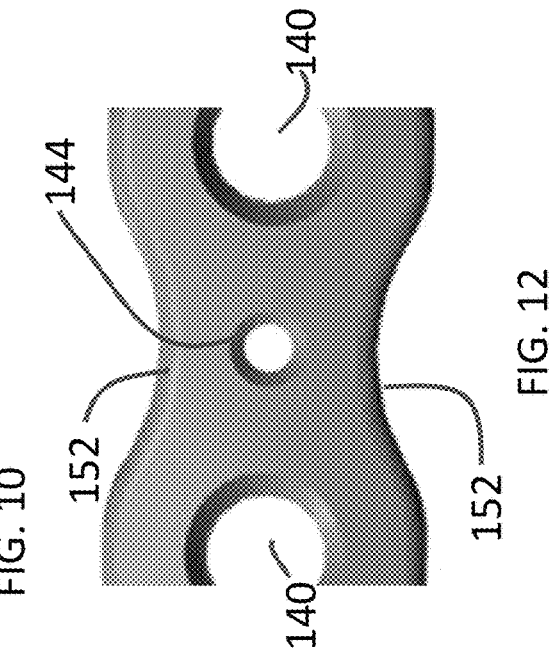
FIG. 12 is an enlarged front elevational view of a portion of the superior end of the bone plate of FIG. 1 showing a K-wire slot.

Side relief cuts, or bending scallops 152, shown in FIGS. 4 and 12, are provided in the sides of the plate 102 on either side of the longitudinal axis L2 and are another means of reducing the moment of inertia between screw holes 140 to allow preferential bending between the screw holes 140, helping to minimize deformation of the screw holes 140. The bending scallops 152 are present along the shaft portion 110 where contour customization by bending the plate 102 is the most likely to be desired.

Figures 13, 14, 15:
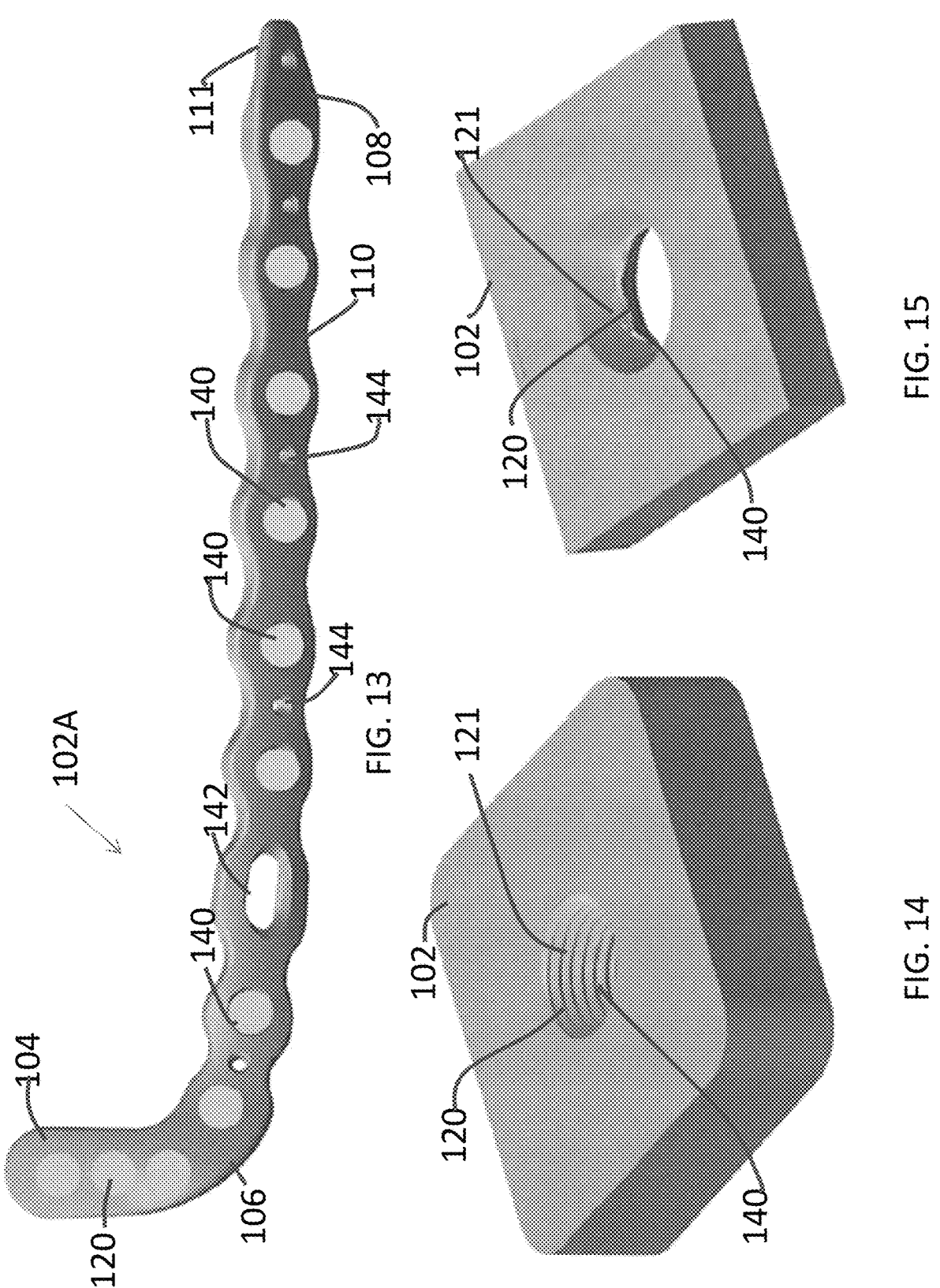
FIG. 13 is a top perspective view of an alternative bone plate in accordance with some embodiments.
FIG. 14 is a top perspective view of a locking bone plate through hole in accordance with some embodiments.
FIG. 15 is a top perspective view of a polyaxial bone plate through hole in accordance with some embodiments.

While bone plate 102 is shown having two row of through holes 120, 121, those skilled in the art will recognize that a bone plate 102A, shown in FIG. 13, can include only a single row of through holes 120.

Further, as shown in FIGS. 14 and 15, the through holes 120, 121, 140 in plates 102/102A can be threaded (FIG. 14) to accept threaded locking fasteners or unthreaded (FIG. 15) to accept polyaxial screws. Additionally, the through holes 120, 121 can be 2.5 mm or 3.5 mm in diameter, while the through holes 140 are typically 3.5 mm in diameter, although other suitable dimensions may be contemplated.

Figure 16:
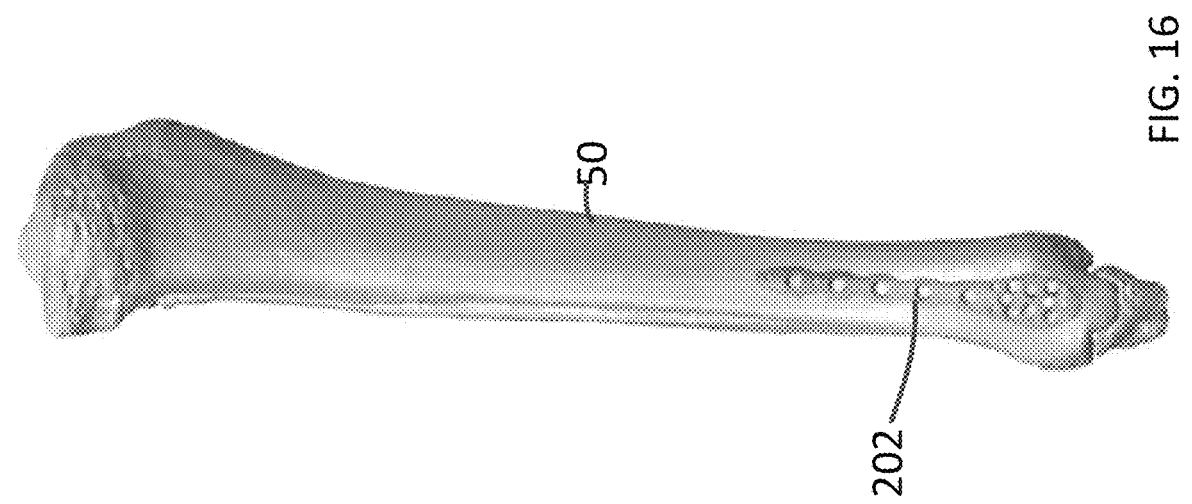
FIG. 16 is a front perspective view of an alternative bone plate assembly in accordance with some embodiments attached to a tibia.
Figures 18, 19:
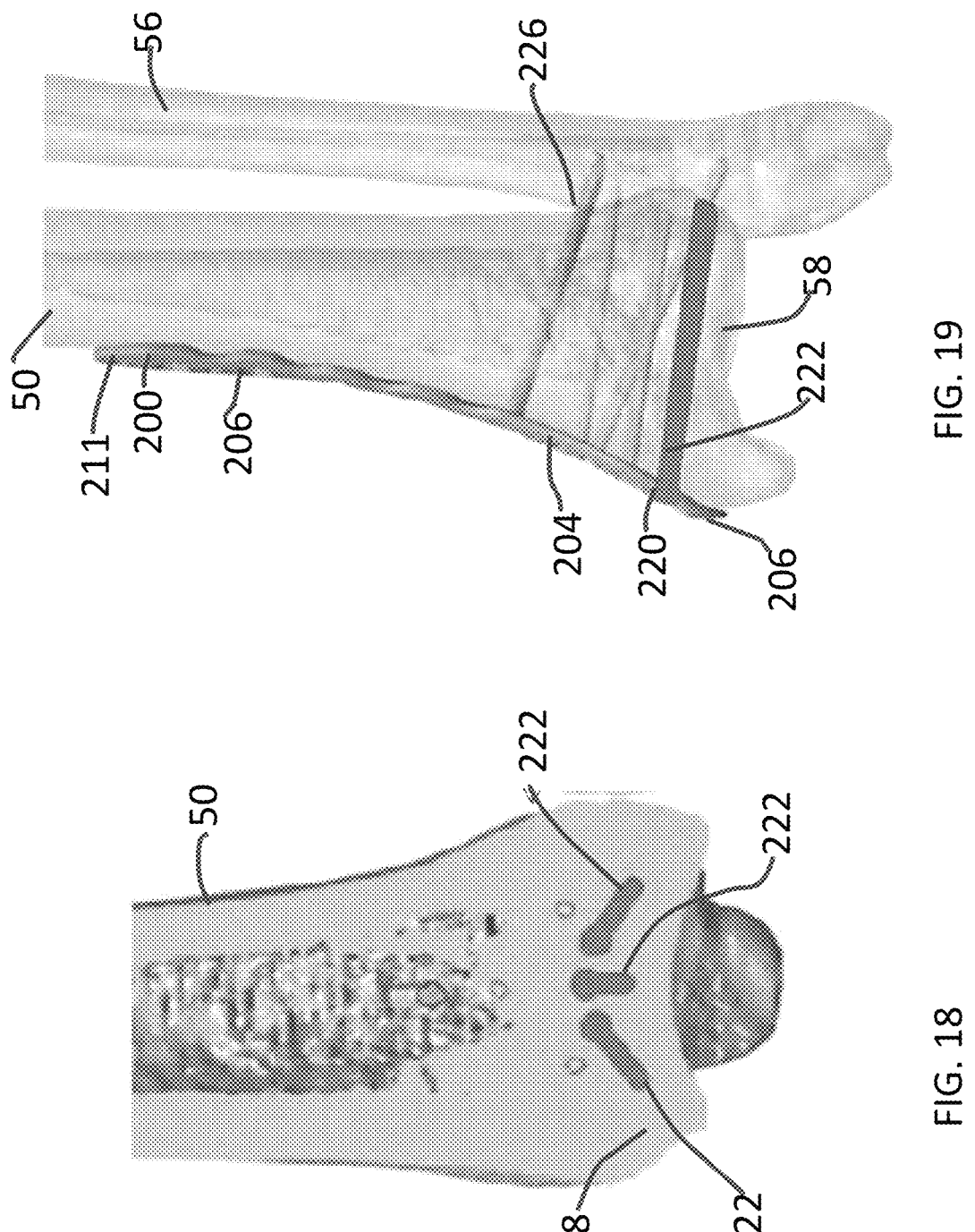
FIG. 18 is a sectional view of the inferior portion of the tibia of FIG. 16, showing screws from the bone plate assembly of FIG. 17.
FIG. 19 us a side elevational view of the bone plate assembly and tibia of FIG. 16.

FIGS. 16-26 disclose a bone plate system 200 ("system 200") in accordance with a second embodiment. System 200 includes a medial bone plate 202 that is contoured to fit along the medial portion of the tibia 50 (FIGS. 16 and 19). Bone plate 202 of system 200 is specific to the left and right tibia. The medial distal tibia 50 is an area of little soft tissue coverage and is by far one of the most challenging areas to treat pilon fractures from. The thickness of the plate 202 is minimal to reduce soft tissue irritation and failure.

Figure 17:
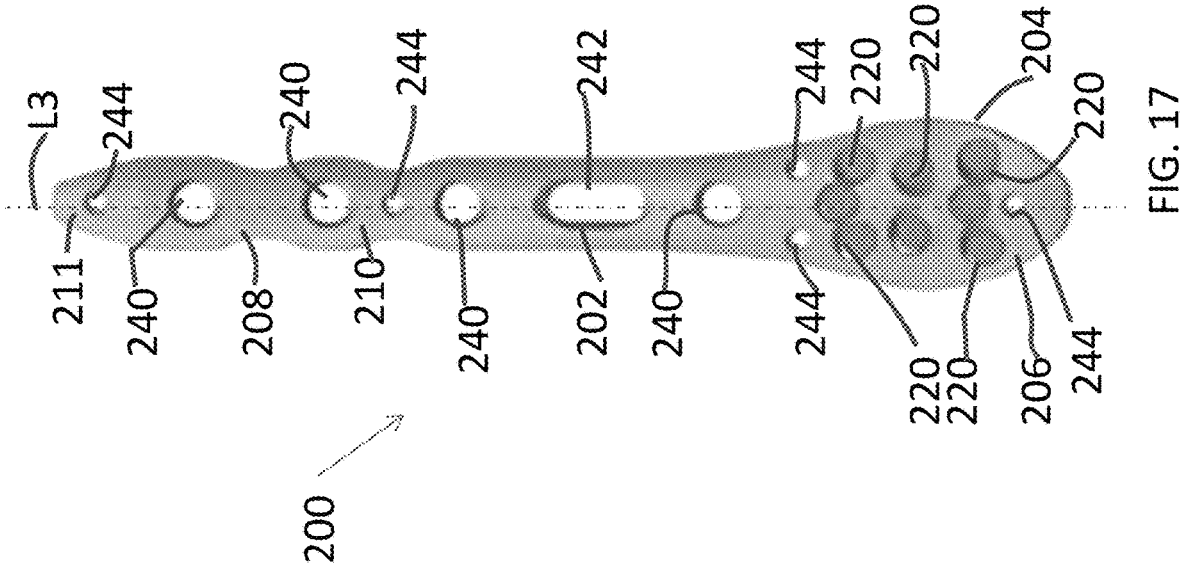
FIG. 17 is a front elevational view of the bone plate assembly of FIG. 16.

Referring to FIG. 17 the bone plate 202 has a plurality of through holes formed therein for receiving fasteners, wherein at least some of the fasteners received therein are locking fasteners. The bone plate 202 comprises an inferior end 204 having a base portion 206 and a superior end 208 having a shaft portion 210. The bone plate 202 has a curvature as shown in FIG. 19, to accommodate the curvature of the inferior end of the tibia 50.

The body 202 extends along a longitudinal axis L3. In some embodiments, the inferior end 204 is chamfered around its perimeter. Advantageously, the contour and chamfer of the inferior end 204 helps to position the bone plate 202 to minimize soft tissue irritation. In some embodiments, the base portion 206 will be placed on a bone member (e.g., tibia) near an articular surface. Certain features of the base portion 206 are advantageously designed to prevent or resist subsidence of an articular surface. The base portion 206 is the widest portion of the plate 202.

In an exemplary embodiment, as shown in FIG. 17, the base portion 206 features a plurality of screw holes 220. The three (3) most inferior screw holes 220 accommodate polyaxial screws 222 and are oriented such that the screws 222 match the contour of the talar dome 58, also known as the plafond. See FIG. 18.

Figures 20, 21:
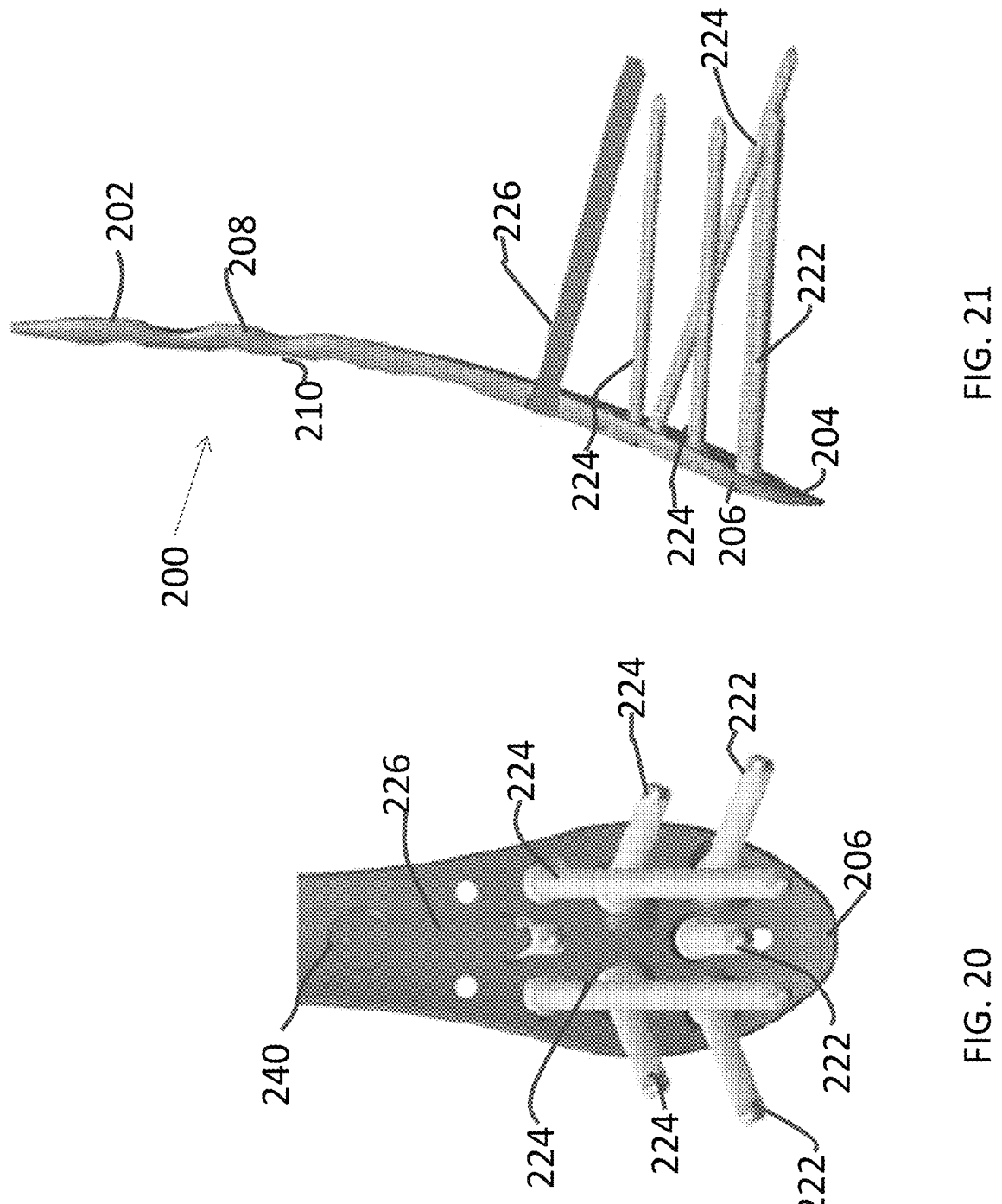
FIG. 20 is a rear elevational view of the base portion of the bone plate assembly of FIG. 16.
FIG. 21 is a side elevational view of the bone plate assembly of FIG. 16.

The remaining distal screws 224 diverge from each other to increase the working width of the plate 202, as shown in FIG. 20. This feature is beneficial for capturing both anterior bone fragments as well as posterior fragments, providing support to the articular block.

Referring to FIG. 20, the two outer most superior screws 224 are angled in an inferior direction to provide additional support of the articular block. The screws 224 also provide support for axial loading. In an exemplary embodiment, screw holes 220 are sized to accept 2.5 mm screws 222, 224.

Referring to FIGS. 20 and 21, the first screw hole 240 on the shaft portion 210 of the plate 202 closest to the base portion 206 supports a kickstand screw 226. The kickstand screw 226 crosses the fracture line of the tibia 50 and helps connect the articular block to the shaft of the tibia 50. In an exemplary embodiment, the screw holes 240 are sized to accept a 3.5 mm screw 226.

Referring back to FIG. 17, the shaft portion 210 is connected to the base portion 206 along axis L3. A plurality of polyaxial through holes 240 extend along the length of the shaft portion 210 and accept locking and non-locking screws, both inserted within a cone of angulation. At least four holes 240 are provided and are sized to accept 3.5 mm screws.

The most superior portion of the shaft portion 210 further comprises a tapered tip 211. In some embodiments, the tapered tip 211 serves as an insertion tip that allows the plate 202 to be inserted beneath skin to a surgical site. The bone plate 202 can be positioned adjacent to bone (e.g., a tibia), whereby the plate 202 can be fixed to the bone. In some embodiments, the tapered tip 211 allows for simplified submuscular plate insertion to minimize incision length.

Figures 22, 23, 24:
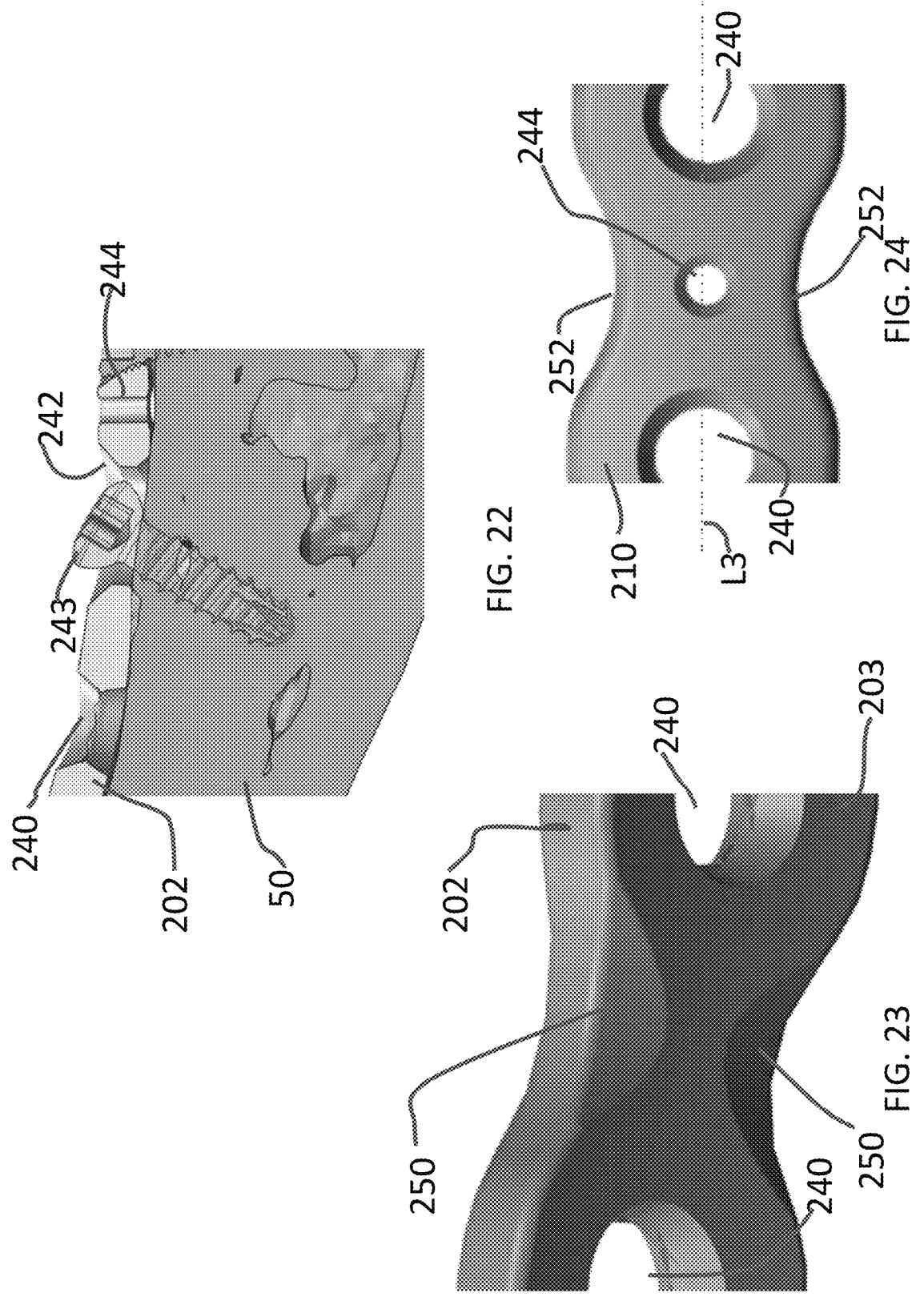
FIG. 22 is a sectional view of a bone with a screw inserted thereinto through a DCP slot in the bone plate of FIG. 16.
FIG. 23 is an enlarged rear perspective view of a portion of the superior end of the bone plate of FIG. 16.
FIG. 24 is a front elevational view of a portion of the superior end of the bone plate of FIG. 16 showing a K-wire slot.

As shown in FIGS. 17 and 22, a dynamic compression plating ("DCP") slot 242 allows lateral motion of the plate 202 relative to the bone to compress a bone fracture. The DCP slot 242 is a through hole that also enables off-axis, or oblique, screw trajectories in the plane of the slot using 3.5 mm non-locking screws 243. Alternatively, 4.0 mm cancellous screws enable oblique or neutral screw trajectories through the DCP slot 242, which can be useful for fragment capture or load neutralization across the fracture line. In some embodiments, the DCP slot 242 has a length that is greater than a length of any of the other holes 220, 240 that receive bone screws therein. In some embodiments, the DCP slot 242 has a length that is at least twice the length of a length of any of the other holes 240, 242 that receive bone screws therein.

K-wire through holes 244 are placed along the length of the plate 202, typically on either side of a through hole 240, to provide provisional fixation. The holes 244 allow for a 1.6 mm K-wire to be placed provisionally.

Referring to FIG. 23, cylindrical undercuts 250 are formed on the rear surface 203 of the plate 202 between adjacent screw holes 240 to help reduce the moment of inertia between adjacent screw holes 240 to allow preferential bending between the holes 240, thereby helping to minimize deformation of the screw holes 240. This feature is useful for contour customization of the plate 202. In some embodiments, the undercuts 250 minimize impact to the periosteal blood supply.

Side relief cuts, or bending scallops 252, shown in FIG. 24, are provided in the sides of the plate 202 on either side of the longitudinal axis L3 and are another means of reducing the moment of inertia between screw holes 240 to allow preferential bending between the screw holes 240, helping to minimize deformation of the screw holes 240. The bending scallops 252 are present along the shaft portion 210 where contour customization by bending the plate 202 is the most likely to be desired.

Figure 25:
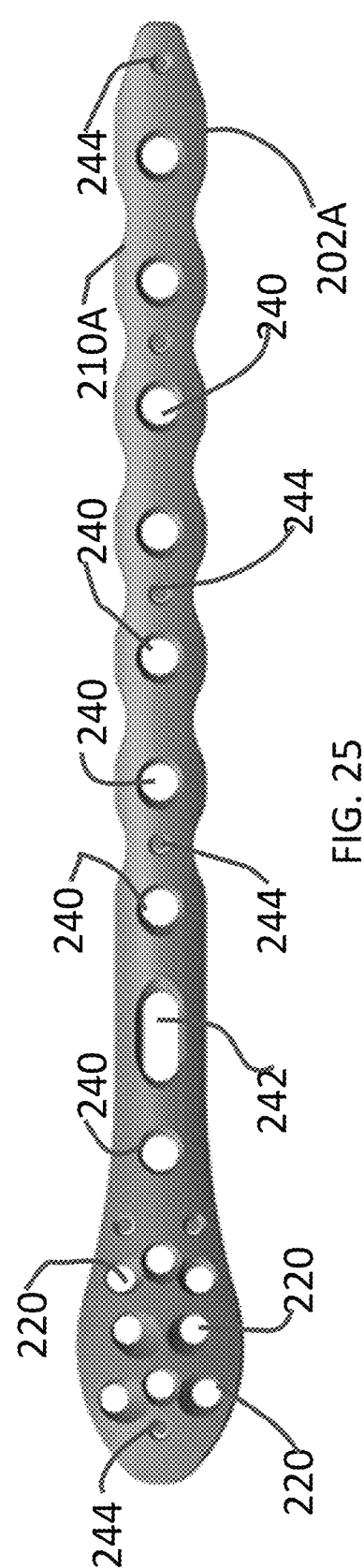
FIG. 25 is a front elevational view of an alternative bone plate in accordance with some embodiments.

While FIG. 17 shows the plate 202 having four (4) through holes 240 extending along the shaft portion 210, for larger patients, a plate 202A, shown in FIG. 25, can be used. The plate 202A has a longer shaft portion 210A than the shaft portion 210, and includes eight through holes 240, instead of the four (4) through holes 240 in the shaft portion 210. The shaft portion 210A also has a single DCP slot 242.

Figure 26:
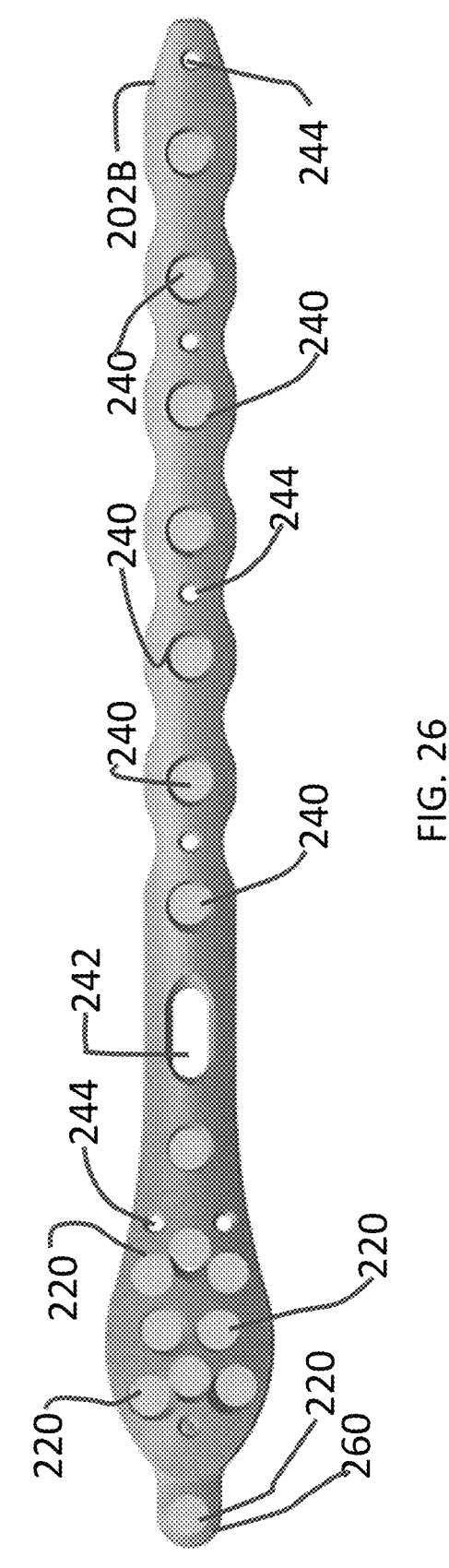
FIG. 26 is a front elevational view of an alternative bone plate in accordance with some embodiments.

FIG. 26 shows an alternative plate 202B that includes a medial malleolus tab 260 that extends inferiorly of the base portion 206. The medial malleolus tab 260 includes a through hole 240 formed therein.

Similar to the through holes 120, 121, 140 in the plate 102 discussed above, the through holes 220, 240 in the plate 202 can be threaded (see FIG. 14) to accept threaded locking fasteners or unthreaded (see FIG. 15) to accept polyaxial screws. Additionally, the through holes 220 can be 2.5 mm or 3.5 mm in diameter, while the through holes 240 are typically 3.5 mm in diameter.

Figure 28:
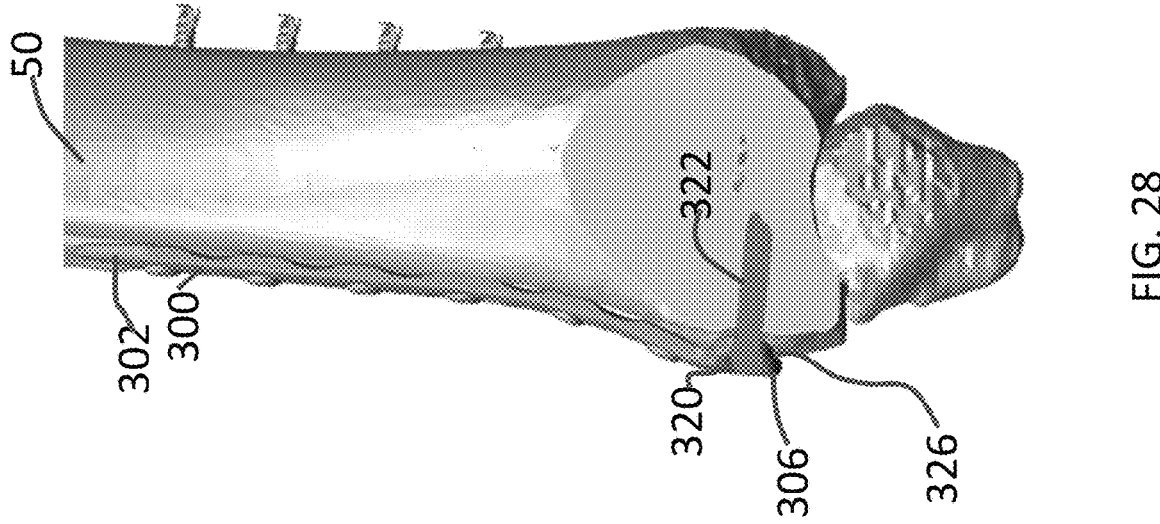
FIG. 28 is a side elevational view of the bone assembly and tibia, partially in section, of FIG. 27.
Figure 27:
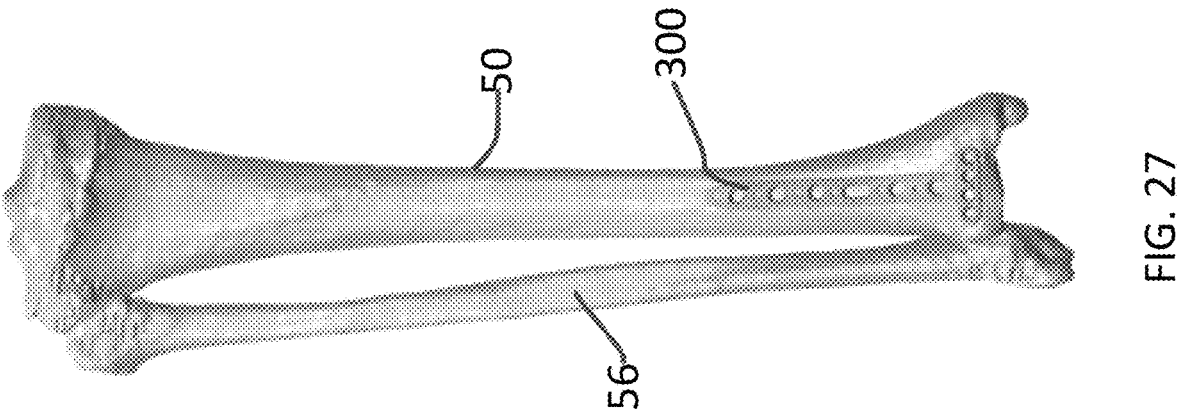
FIG. 27 front elevational view of an alternative bone plate assembly in accordance with some embodiments attached to a tibia.

FIGS. 27-33 disclose a bone plate system 300 ("system 300") in accordance with a third embodiment. System 300 includes a posterior bone plate 302 that is contoured to fit along the posterior portion of the tibia 50 (FIGS. 27 and 28). Bone plate 302 of system 300 is interchangeable for left-leg and right-leg tibias 50.

Figures 29, 30:
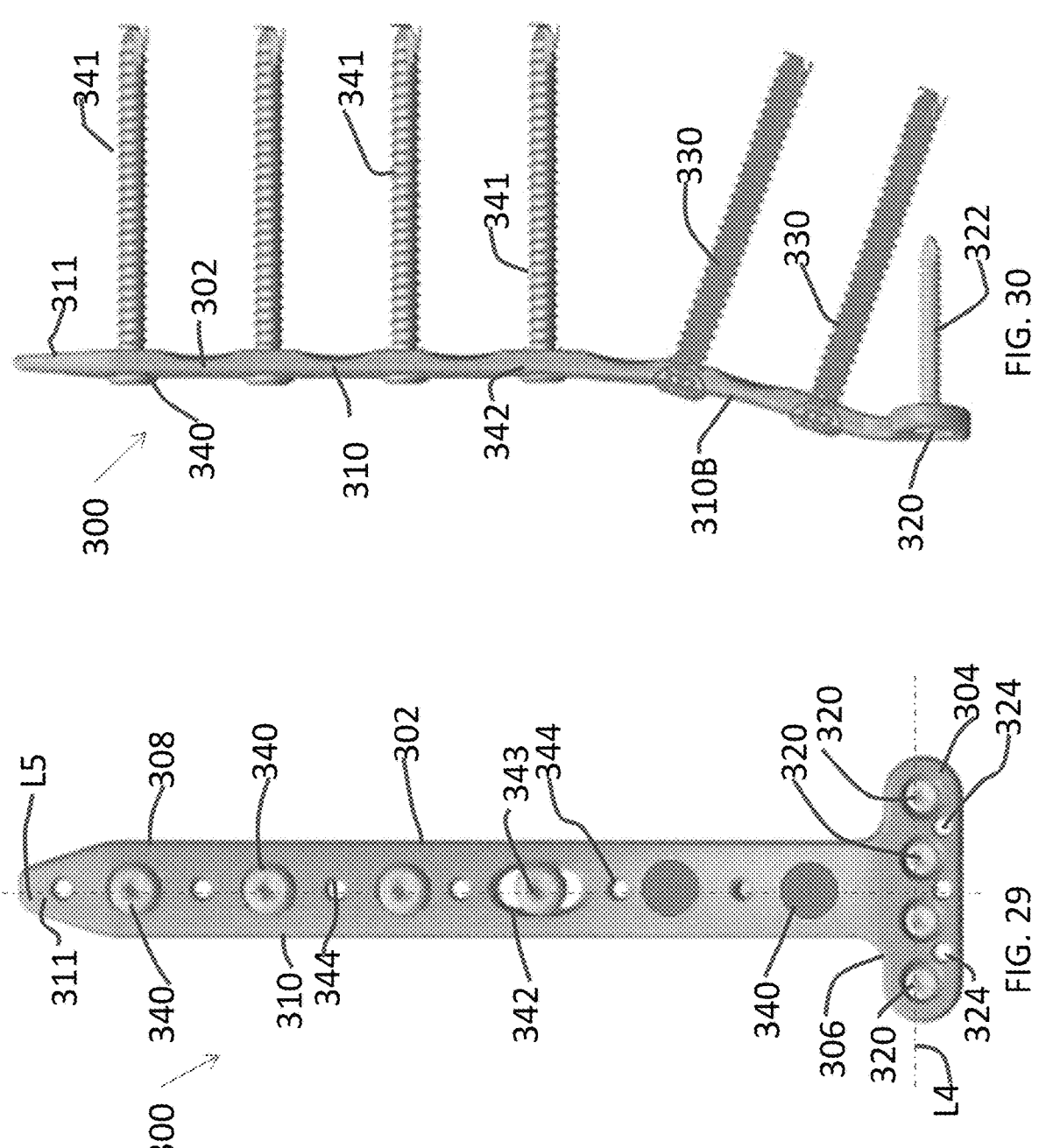
FIG. 29 is a front elevational view of the bone plate assembly of FIG. 27.
FIG. 30 is a side elevational view of the bone plate assembly of FIG. 29.

Referring to FIGS. 29 and 30, the bone plate 302 has a plurality of through holes formed therein for receiving fasteners, wherein at least some of the fasteners received therein are locking fasteners. The bone plate 302 comprises an inferior end 304 having a base portion 306 and a superior end 308 having a shaft portion 310. As shown in FIG. 30, the bone plate 302 is multi-planar, with the most superior end of the shaft portion 310 extending generally in a singular plane, while the most inferior end of the shaft portion 310 is curved away from the plane and extends across more than one plane. The curvature of the most inferior end of the shaft portion 310 relative to the most superior end of the shaft portion 310 can be adjusted to match the anatomy of a particular patient.

The base portion 306 extends along a first longitudinal axis L4. In some embodiments, the inferior end 304 is chamfered around its perimeter. Advantageously, the contour and chamfer of the inferior end 304 helps to position the bone plate 302 to minimize soft tissue irritation. In some embodiments, the base portion 306 will be placed on a bone member (e.g., tibia) near an articular surface. Certain features of the base portion 306 are advantageously designed to prevent or resist subsidence of an articular surface.

In an exemplary embodiment, as shown in FIG. 29, the base portion 306 features a single row of four (4) 2.5 mm polyaxial screw holes 320. These holes 320 are through holes for receiving polyaxial screws 322 that are mostly commonly placed uni-cortical (See FIG. 28). The function of the screws 322 is to support the posterior malleolus fragments and provide a secure block to which to fasten the anterior fragments.

As shown in FIG. 29, the most inferior edge of the base portion 306 further comprises one or more novel multi-purpose holes 324. The multi-purpose holes 324 are smaller than the holes 320. In some embodiments, the multi-purpose holes 324 enable passage of suture/needles to serve as anchor points useful for reattachment and repositioning of soft tissue damaged during surgery. This may aid post-surgical soft tissue healing. The multi-purpose holes 324 also allow for a non-threaded 1.6 mm K-wire (not shown) to be provisionally placed. As shown in FIG. 28, one or more undercuts 326 advantageously allow access to one or more sutures through the bone plate 302 even after the bone plate 302 is implanted on bone. The sutures can be used to attach the bone plate 302 to adjacent tissue, thereby further securing the bone plate 302 at or near a surgical site.

Referring back to FIGS. 29 and 30, the shaft portion 310 is connected to the base portion 306. The shaft portion 310 extends along a second axis L5, extending generally orthogonally to the first axis L4. A plurality of polyaxial through holes 340 extend along the length of the shaft portion 310 and accept locking and non-locking screws, both inserted within a cone of angulation. At least six holes 340 are provided and are sized to accept 3.5 mm screws 341. Additionally, referring to FIG. 30, the plate system 300 features two kickstand screws 330 that cross the fracture line and help connect the articular block to the shaft. The kickstand screws 330 are located in the two most inferior holes 340 and are proximal to the base portion 306.

The most superior portion of the shaft portion 310 further comprises a tapered tip 311. In some embodiments, the tapered tip 311 serves as an insertion tip that allows the plate 302 to be inserted beneath skin to a surgical site. The bone plate 302 can be positioned adjacent to bone (e.g., a tibia), whereby the plate 302 can be fixed to the bone. In some embodiments, the tapered tip 311 allows for simplified submuscular plate insertion to minimize incision length.

Figures 31, 32:
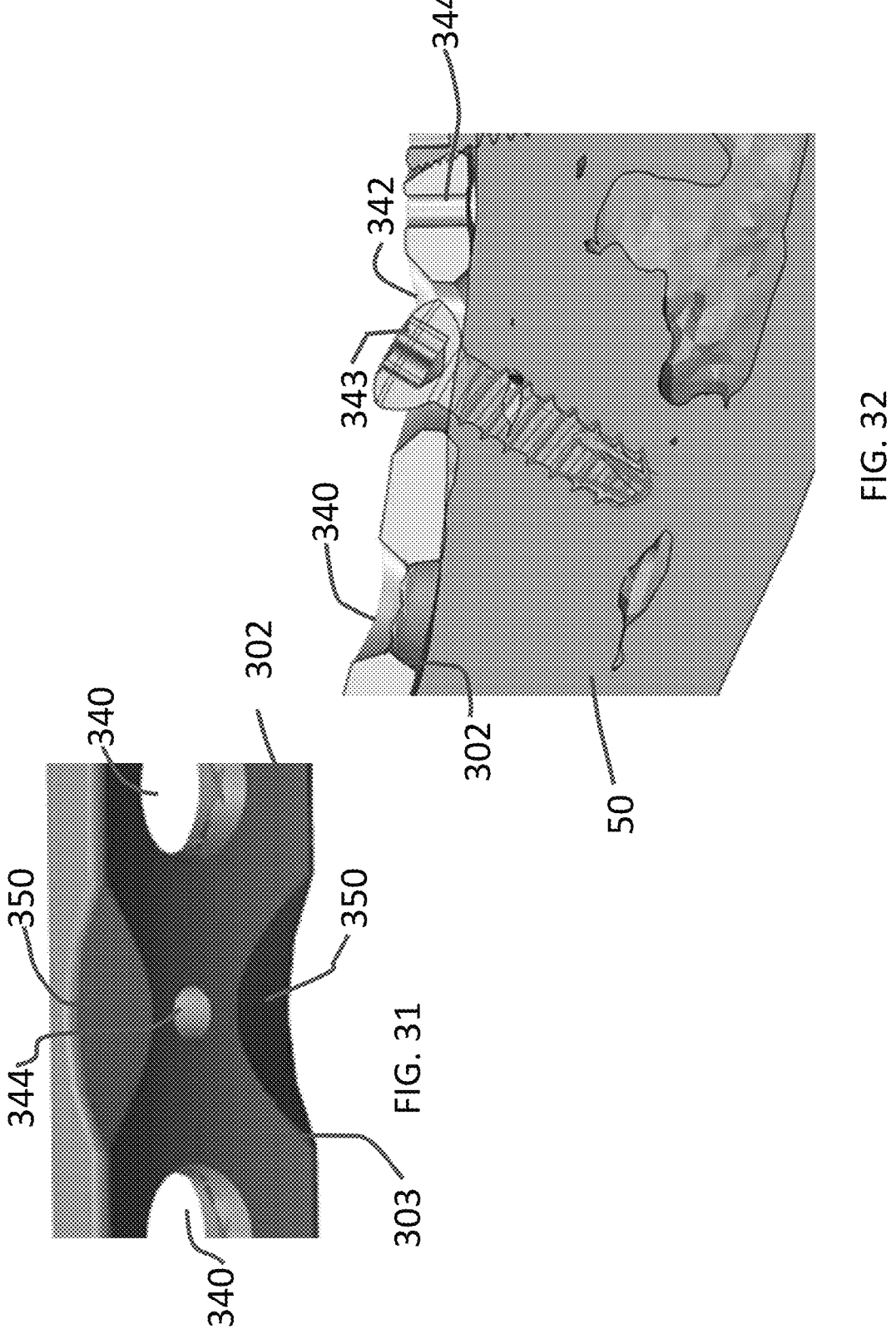
FIG. 31 is an enlarged rear perspective view of a portion of the superior end of the bone plate of FIG. 29.
FIG. 32 is a sectional view of a bone with a screw inserted thereinto through a DCP slot in the bone plate of FIG. 27.

As shown in FIGS. 29 and 32, a DCP slot 342 allows lateral motion of the plate 302 relative to the bone to compress a bone fracture. 3.5 mm non-locking screws 343 are used for this technique as well as standard neutral placement in the center of the slot 342. The DCP slot 342 is a through hole that also enables off-axis, or oblique, screw trajectories in the plane of the slot using 3.5 mm non-locking screws 343, as shown in FIG. 32. Alternatively, 4.0 mm cancellous screws enable oblique or neutral screw trajectories through the DCP slot 342, which can be useful for fragment capture or load neutralization across the fracture line. In some embodiments, the DCP slot 342 has a length that is greater than a length of any of the other holes 320, 340 that receive bone screws therein. In some embodiments, the DCP slot 342 has a length that is at least twice the length of a length of any of the other holes 320, 340 that receive bone screws therein.

K-wire through holes 344 are placed along the length of the shaft portion 310, typically on either side of a through hole 340, to provide provisional fixation. The holes 344 allow for a 1.6 mm K-wire to be placed provisionally.

Referring to FIG. 31, cylindrical undercuts 350 are formed on the rear surface 303 of the plate 302 between adjacent screw holes 340 to help reduce the moment of inertia between adjacent screw holes 340 to allow preferential bending between the holes 340, thereby helping to minimize deformation of the screw holes 340. This feature is useful for contour customization of the plate 302. In some embodiments, the undercuts 350 minimize impact to the periosteal blood supply.

Similar to the through holes 120, 121, 140 in the plate 102 discussed above, the through holes 320, 340 in the plate 302 can be threaded (see FIG. 14) to accept threaded locking fasteners or unthreaded (see FIG. 15) to accept polyaxial screws. Additionally, the through holes 320 can be 2.5 mm or 3.5 mm in diameter, while the through holes 340 are typically 3.5 mm in diameter.

Figure 33:
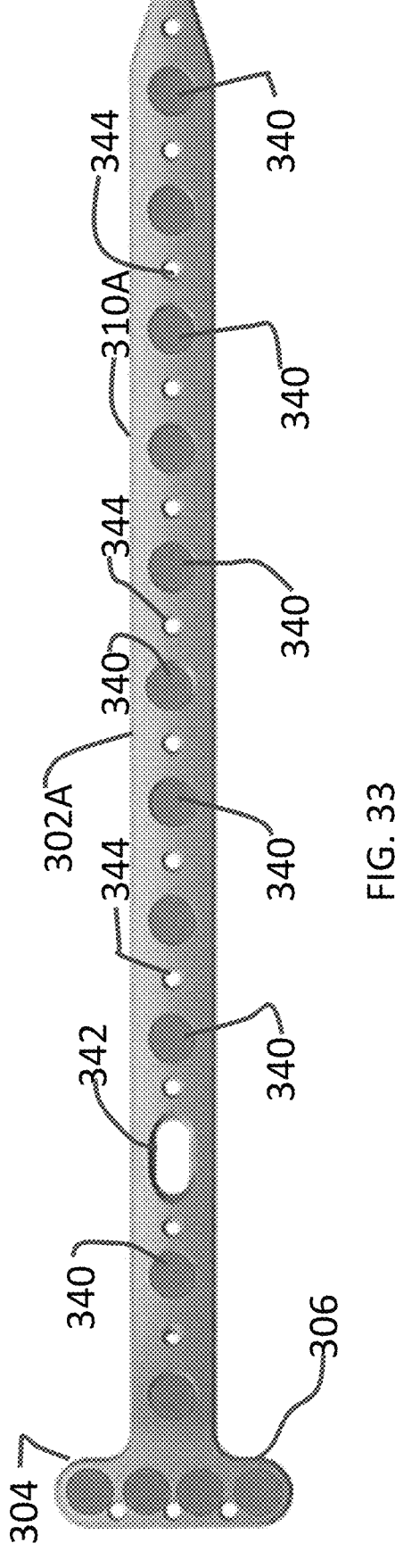
FIG. 33 is a front elevational view of an alternative bone plate in accordance with some embodiments.

While FIG. 29 shows the plate 302 having three through holes 340 extending along the shaft portion 210 superiorly of the DCP slot 342, for larger patients, a plate 302A, shown in FIG. 33, can be used. The plate 302A has a longer shaft portion 310A than the shaft portion 310, and includes nine through holes 340, instead of the four (4) through holes 340 in the shaft portion 310. The shaft portion 310A also has a single DCP slot 342.

Figures 34, 34A, 34B, 34C, 34D:
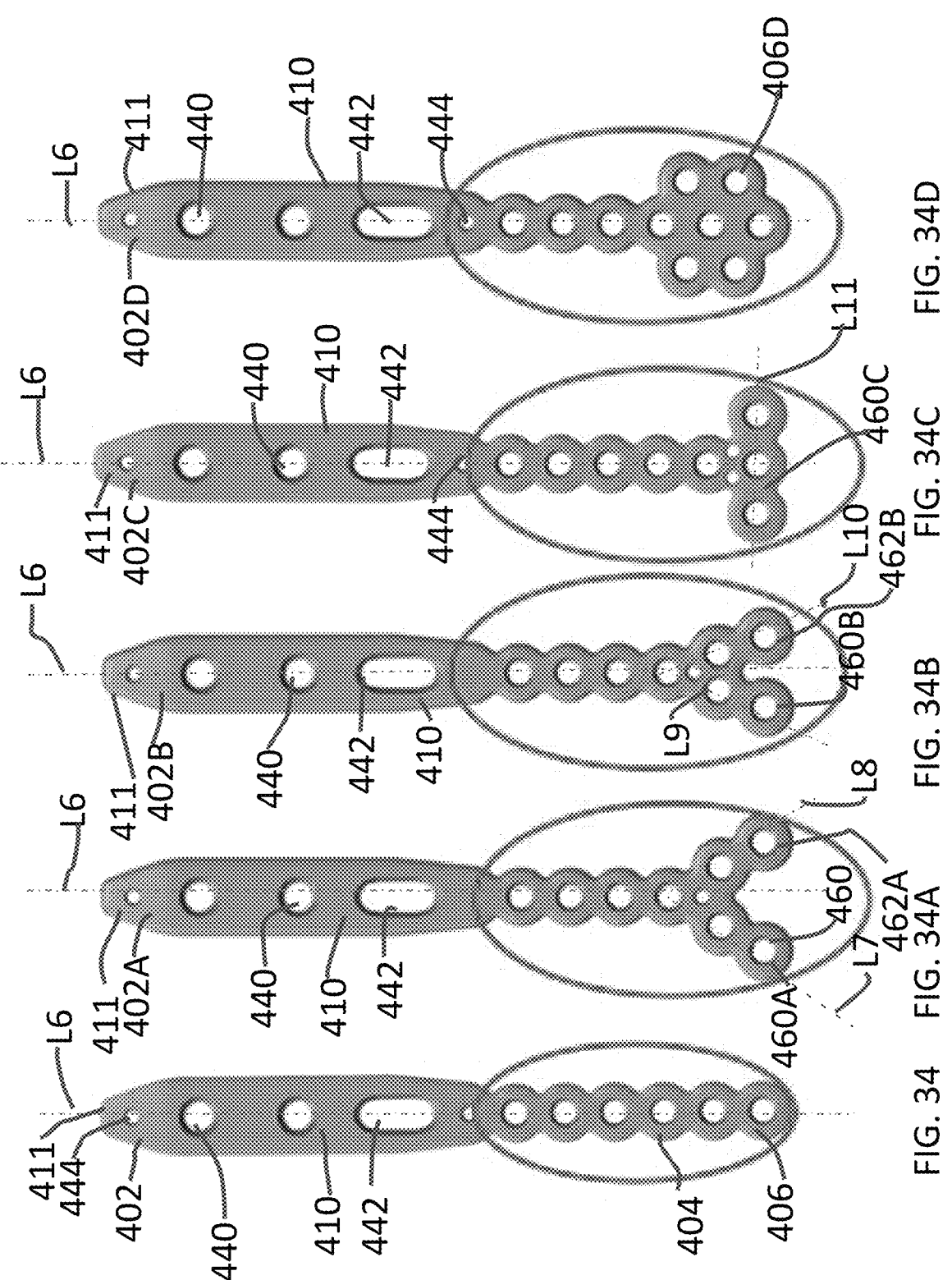
FIG. 34 is a front elevational view of an alternative bone plate in accordance with some embodiments.
FIG. 34A is a front elevational view of an alternative bone plate in accordance with some embodiments.
FIG. 34B is a front elevational view of an alternative bone plate in accordance with some embodiments.
FIG. 34C is a front elevational view of an alternative bone plate in accordance with some embodiments.
FIG. 34D is a front elevational view of an alternative bone plate in accordance with some embodiments.
Figure 36:
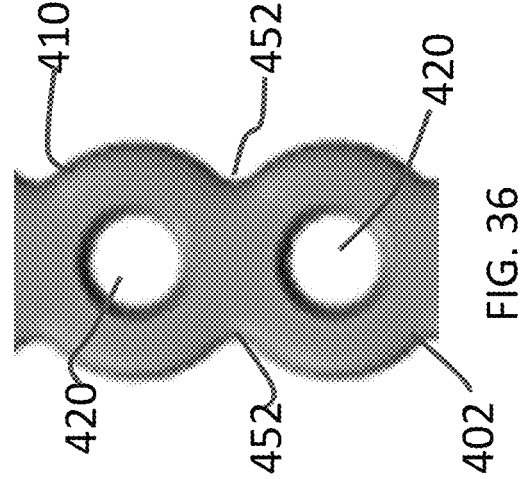
FIG. 36 is an enlarged front elevational view of is a portion of the inferior end of the bone plate of FIG. 34.
Figure 35:
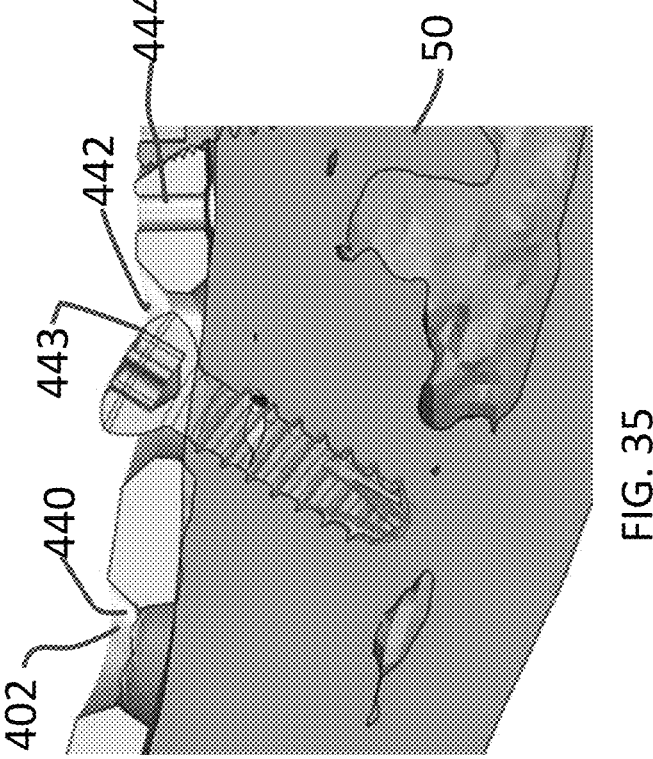
FIG. 35 is a sectional view of a bone with a screw inserted thereinto through a DCP slot in the bone plate of FIG. 34.

FIGS. 34-36 disclose a plurality of metaphyseal bone plates 402-402D in accordance with a fourth embodiment. FIGS. 34-34D show different embodiments of plates 402-402D with a common shaft portion 410, but with different base portions 406-406D.

The plates 402-402D are small and thin in required locations, specifically in the base portion 406-406D of the plates 402-402D. The plates 402-402D have a base portion 406-406D that has a smaller profile than the shaft portion 410 of the plates 402-402D. A benefit of the small profile and thin stock in the base portions 406-406D is the reduced risk of soft tissue irritation and soft tissue failure. The theory behind the plates 402-402D is a design that blends the small mini-fragment plates with the larger small fragment plates. The superior portion 410 is slightly thicker and wider than the inferior base portion 406, which provides the strength necessary to fix shaft fractures.

Referring to FIGS. 34-34D, the shaft portion 410 is connected to each of the different base portions 406-406D. The shaft portion 410 extends along a first axis L6. A plurality of polyaxial through holes 440 extend along the length of the shaft portion 410 and accept locking and non-locking screws, both inserted within a cone of angulation. At least two holes 440 are provided and are sized to accept 3.5 mm screws.

The most superior portion of the shaft portion 410 further comprises a tapered tip 411. In some embodiments, the tapered tip 411 serves as an insertion tip that allows the plate 402-402D to be inserted beneath skin to a surgical site. The bone plate 402-402D can be positioned adjacent to bone (e.g., a tibia), whereby the plate 402-402D can be fixed to the bone. In some embodiments, the tapered tip 411 allows for simplified submuscular plate insertion to minimize incision length.

As shown in FIGS. 34 and 35, a dynamic compression plating ("DCP") slot 442 allows lateral motion of the plate 402 relative to the bone to compress a bone fracture. 3.5 mm non-locking screws 443 are used for this technique as well as standard neutral placement in the center of the slot 442. The DCP slot 442 is a through hole that also enables off-axis, or oblique, screw trajectories in the plane of the slot using 3.5 mm non-locking screws 443, as shown in FIG. 35. Alternatively, 4.0 mm cancellous screws enable oblique or neutral screw trajectories through the DCP slot 442, which can be useful for fragment capture or load neutralization across the fracture line. In some embodiments, the DCP slot 442 has a length that is greater than a length of any of the other holes 420, 440 that receive bone screws therein. In some embodiments, the DCP slot 442 has a length that is at least twice the length of a length of any of the other holes 420, 440 that receive bone screws therein.

K-wire through holes 444 are placed proximate to the tip 411 of the plate 402 as well as proximate to an interface between the shaft portion 410 and the base portion 406-406D, to provide provisional fixation. The holes 444 allow for a 1.6 mm K-wire to be placed provisionally.

Another design feature of the plates 402-402D is the ability to adjust and customize the contour of the base portion 410-410D to match any patient's anatomy. Perimeter scallops 452 aid in bending the plate without distorting the 2.5 mm polyaxial screw through holes 420. In an exemplary embodiment, the through holes 420 are spaced about 7.5 mm apart from adjacent through holes 420 which maximizes the amount of fixation distally.

The plates 402-402D are designed with various shapes/profiles in the base portion 406-406D to accommodate different implantation locations. Plate 402 is a linear plate, wherein the base portion 406 extends along the first axis L6 co-linearly with the shaft portion 410.

Plate 402A is a Y-plate, with a first leg 460 extending along a second axis L7, different from the first axis L6, and a second leg 462 extending along a third axis L8, different from the first axis L6, wherein each of the axes L7 and L8 each extend at an angle of about 30 degrees relative to the axis L6.

Plate 402B is also a Y-plate, with a first leg 460B extending along a second axis L9, different from the first axis L6, and a second leg 462B extending along a third axis L8, different from the first axis L6, wherein each of the axes L7 and L8 each extend at an angle of about 320 degrees relative to the axis L6.

Plate 402C is a T-plate, with a first leg 460C extending along a second axis L10, generally orthogonal to the first axis L6. Plate 402D is a clover plate, with a plurality of 2.5 mm polyaxial screw through holes 420 surrounding a central 2.5 mm polyaxial screw through hole 420.

Each plate 402-402D is optimal for different scenarios. For example, plates 402A, 402B are the perfect shape for the medial distal tibia. The two legs 460B, 462B and 460C, 462C of the Y can be bent to fit around the medial malleolus.

Figure 38:
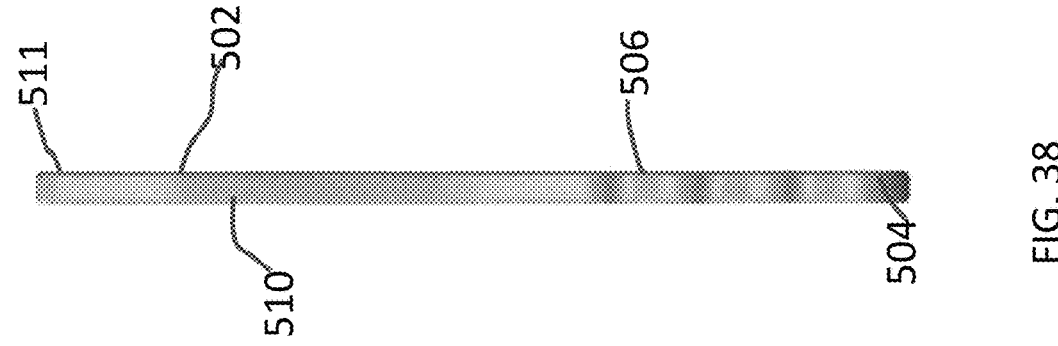
FIG. 38 is a side elevational view of the bone plate of FIG. 37.
Figure 37:
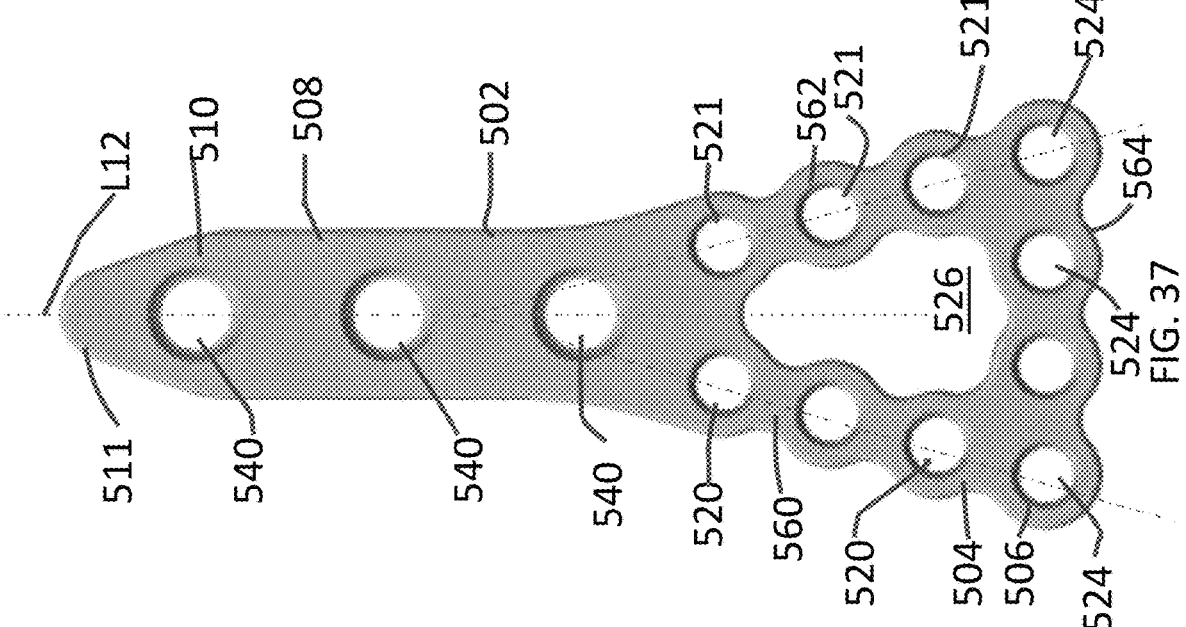
FIG. 37 is a front elevational view of an alternative bone plate in accordance with some embodiments.

FIGS. 37 and 38 disclose an anterior bone plate 502 in accordance with a fifth embodiment. The plate 502 is designed to be placed anterior on the distal tibia (See FIG. 38) and is similar to the metaphyseal plates 402-402D discussed above in the sense that the plate 502 can be modified and customized to fit the anatomy of the anterior tibia. The anterior distal tibia lacks soft tissue coverage, similar to the medial distal tibia. The anterior plate 502 is thin, much like the medial bone plate 202 and the base portion 106 of the anterolateral plate 102.

The bone plate 502 comprises an inferior end 504 having a base portion 506 and a superior end 508 having a shaft portion 510. The bone plate 502 is generally planar, but can be contoured to match a particular patient's anatomy.

The base portion 506 is generally triangular in shape. In some embodiments, the inferior end 504 is chamfered around its perimeter. Advantageously, the contour and chamfer of the inferior end 504 helps to position the bone plate 502 to minimize soft tissue irritation. In some embodiments, the base portion 506 will be placed on a bone member (e.g., tibia) near an articular surface. Certain features of the base portion 506 are advantageously designed to prevent or resist subsidence of an articular surface.

In an exemplary embodiment, as shown in FIG. 37, the base portion 506 features two (2) rows of three (3) 3.5 mm screw holes 520, 521, each row extending along a respective leg 560, 562. The holes 520, 521 are through holes for receiving screws that are closest to an articular surface of a joint. The holes 520, 521 can be locking holes or polyaxial holes. The polyaxial holes accept locking and non-locking screws, both inserted within a cone of angulation. Each leg 560, 562 extends at an angle of about 15 degrees relative to a shaft longitudinal axis L12.

A connecting portion 564 connects the inferior most ends of the legs 560, 562 to each other. The connecting portion 564 includes a row of four (4) 2.5 mm polyaxial screw holes 524. A cavity 526 is provided between the legs 560, 562 and the connecting portion 564.

By providing three (3) sets of holes 520, 521, 524, the bone plate 502 advantageously accommodates a greater number of screws, thereby providing greater support near the joint.

The shaft portion 510 is connected to the base portion 506. The shaft portion 510 extends along the axis L12. A plurality of polyaxial through holes 540 extend along the length of the shaft portion 510 and accept locking and non-locking screws, both inserted within a cone of angulation. At least three (3) holes 540 are provided and are sized to accept 3.5 mm screws.

The most superior portion of the shaft portion 510 further comprises a tapered tip 511. In some embodiments, the tapered tip 511 serves as an insertion tip that allows the plate 502 to be inserted beneath skin to a surgical site. The bone plate 502 can be positioned adjacent to bone (e.g., a tibia), whereby the plate 502 can be fixed to the bone. In some embodiments, the tapered tip 511 allows for simplified submuscular plate insertion to minimize incision length.

Figure 40:
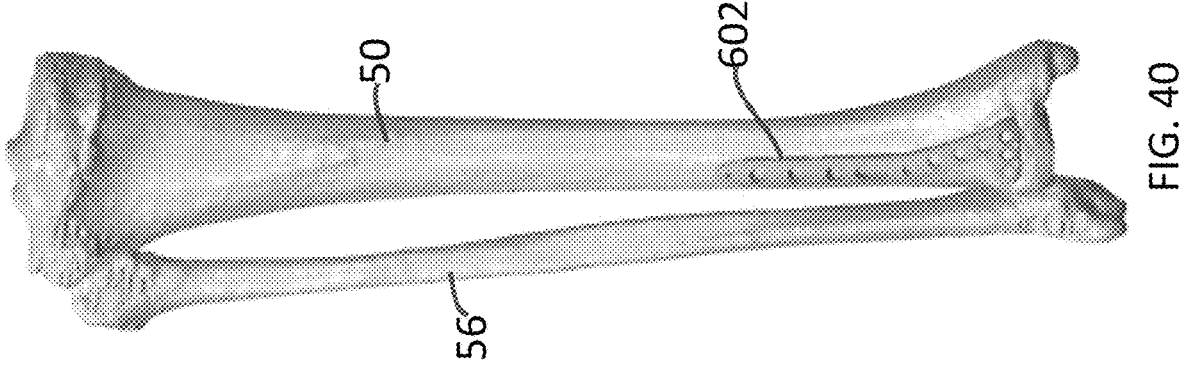
FIG. 40 is a front perspective view of the bone plate of FIG. 39 attached to a tibia.
Figure 39:
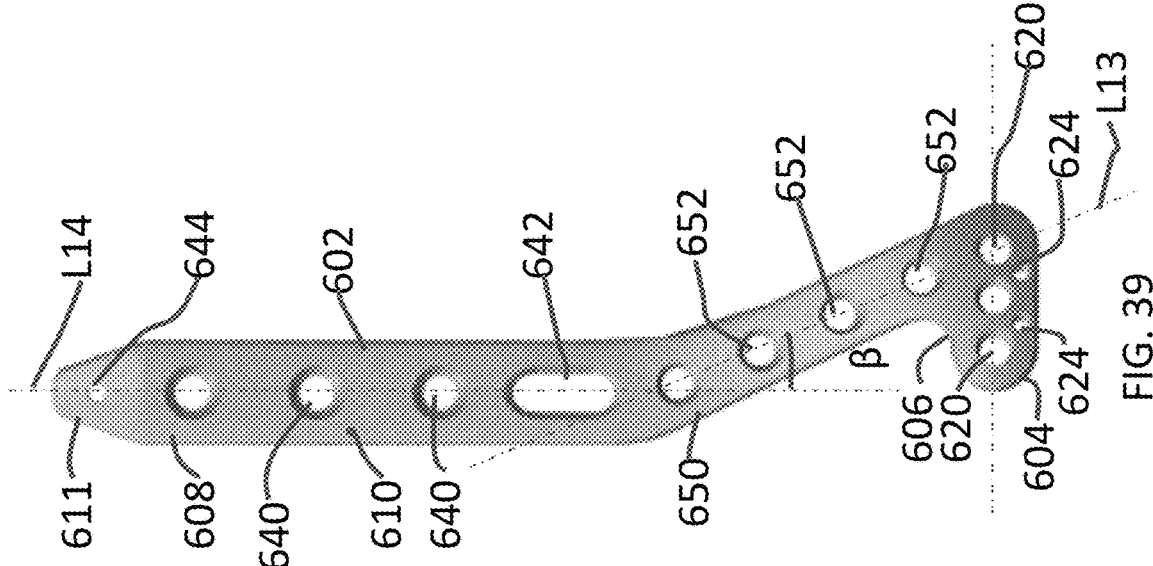
FIG. 39 is a front elevational view of an alternative bone plate in accordance with some embodiments.

FIGS. 39 and 40 disclose a posterolateral bone plate 602 in accordance with a sixth embodiment. The plate 602 is designed to address a posterior fracture of the tibia 50, as shown in FIG. 40.

Referring to FIG. 39, the bone plate 602 comprises an inferior end 604 having a base portion 606 and a superior end 608 having a shaft portion 610. The base portion 606 extends along a first longitudinal axis L13. In some embodiments, the inferior end 604 is chamfered around its perimeter. Advantageously, the contour and chamfer of the inferior end 604 helps to position the bone plate 602 to minimize soft tissue irritation. In some embodiments, the base portion 606 will be placed on a bone member (e.g., tibia 50) near an articular surface. Certain features of the base portion 606 are advantageously designed to prevent or resist subsidence of an articular surface.

In an exemplary embodiment, as shown in FIG. 39, the base portion 306 features a single row of three (3) 2.5 mm co-linear screw holes 620. The holes 620 are through holes for receiving screws that are closest to an articular surface of a joint. The holes 620 can be locking holes or polyaxial holes. The polyaxial holes accept locking and non-locking screws, both inserted within a cone of angulation.

The most inferior edge of the base portion 606 further comprises one or more novel multi-purpose holes 624. The multi-purpose holes 624 are smaller than the holes 620. In some embodiments, the multi-purpose holes 624 enable passage of suture/needles to serve as anchor points useful for reattachment and repositioning of soft tissue damaged during surgery. This may aid post-surgical soft tissue healing. The multi-purpose holes 624 also allow for a non-threaded 1.6 mm K-wire to be provisionally placed.

The shaft portion 610 is connected to the base portion 606. The shaft portion 610 extends along a second axis L14, different from the first axis L13. A plurality of polyaxial through holes 640 extend along the length of the shaft portion 610 and accept locking and non-locking screws, both inserted within a cone of angulation. At least three (3) holes 640 are provided and are sized to accept 3.5 mm screws.

The most superior portion of the shaft portion 610 further comprises a tapered tip 611. In some embodiments, the tapered tip 611 serves as an insertion tip that allows the plate 602 to be inserted beneath skin to a surgical site. The bone plate 602 can be positioned adjacent to bone (e.g., a tibia), whereby the plate 602 can be fixed to the bone. In some embodiments, the tapered tip 611 allows for simplified submuscular plate insertion to minimize incision length.

As shown in FIG. 39, a DCP slot 642 allows lateral motion of the plate 102 relative to the bone to compress a bone fracture. 3.5 mm non-locking screws (not shown) are used for this technique as well as standard neutral placement in the center of the slot 642. The DCP slot 642 is a through hole that also enables off-axis, or oblique, screw trajectories in the plane of the slot using 3.5 mm non-locking screws. Alternatively, 4.0 mm cancellous screws enable oblique or neutral screw trajectories through the DCP slot 642, which can be useful for fragment capture or load neutralization across the fracture line. In some embodiments, the DCP slot 642 has a length that is greater than a length of any of the other holes 620, 640 that receive bone screws therein. In some embodiments, the DCP slot 642 has a length that is at least twice the length of a length of any of the other holes 620, 640 that receive bone screws therein.

A K-wire through hole 644 is located at the superior end of the shaft portion 608, proximate to the tip 611, to provide provisional fixation. The hole 644 allows for a 1.6 mm K-wire to be placed provisionally.

An inferior part 650 of shaft portion 610 connects the DCP slot 642 to the base portion 606. Inferior part 650 is angled with respect to axis L13 by an angle R of about 22 degrees. Inferior part 650 includes a plurality of polyaxial through holes 652 extend along the length of the inferior part 650 and accept locking and non-locking screws, both inserted within a cone of angulation. At least three (3) holes 652 are provided and are sized to accept 2.5 mm screws. In the embodiment shown in FIG. 39, four (4) holes 652 are provided.

While some embodiments of plates 102-602 according to exemplary embodiments are shown with screws, while other plates 102-602 are not, those skilled in the art will recognize that all screw holes x20, x21, x40, x42 can include suitable screws of the screws described herein.

In accordance with one embodiment, a method of treating or fixing fractures and/or non-unions of the distal tibia may include providing one or more of the trauma plates to the affected region and securing the plate thereto. In particular, the method for repairing a bone fracture or non-union may include providing a bone plate or kit of bone plates having different sizes, shapes, or configurations, selecting the appropriate bone plate, positioning the bone plate adjacent to the affected area, and securing the bone plate to the bone or bone portions.

Turning now to FIGS. 41A-46C, one or more embodiments of targeting nominal trajectories of distal holes of the anterolateral, wide anterolateral and medial plates, such as those discussed above, are illustrated. Nominal trajectories may refer to pre-set trajectories for inserting bone screws into a bone that a user of a bone plate assembly may use. As noted above, bone plates consistent with the present disclosure may be polyaxial holes which may provide a user with flexibility regarding the trajectory to insert bone screws into the bone plate. A guide block, commonly known as a backpack, may attach to an implant and target nominal trajectories to the extent that the user prefers to use a pre-set trajectory instead of independently setting a trajectory in the polyaxial hole of the bone plate without use of the backpack. The backpack may be placed onto the implant and locked into place via an attachment screw.

Figure 41B:
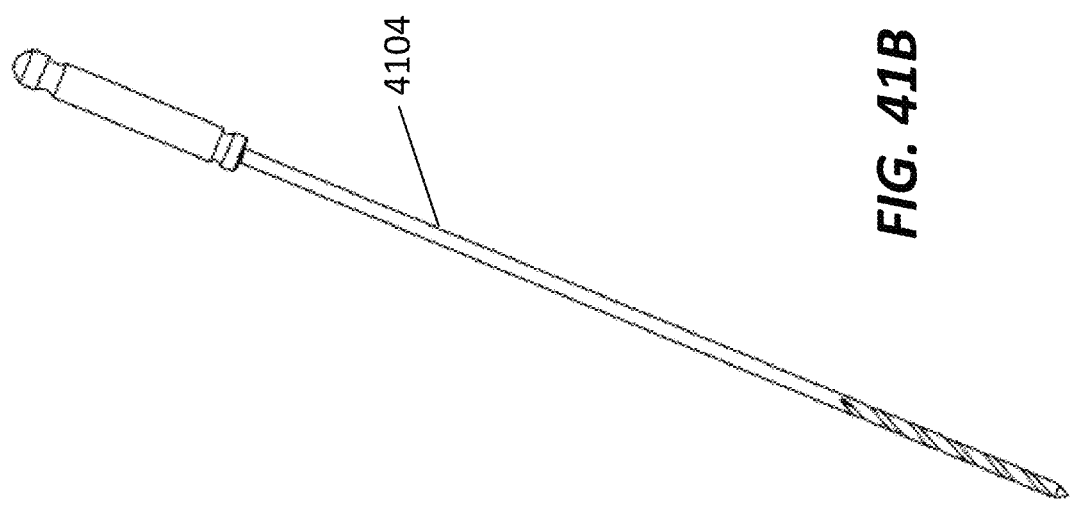
FIG. 41B illustrates an exemplary drill bit consistent with the principles of the present disclosure.
Figure 41A:
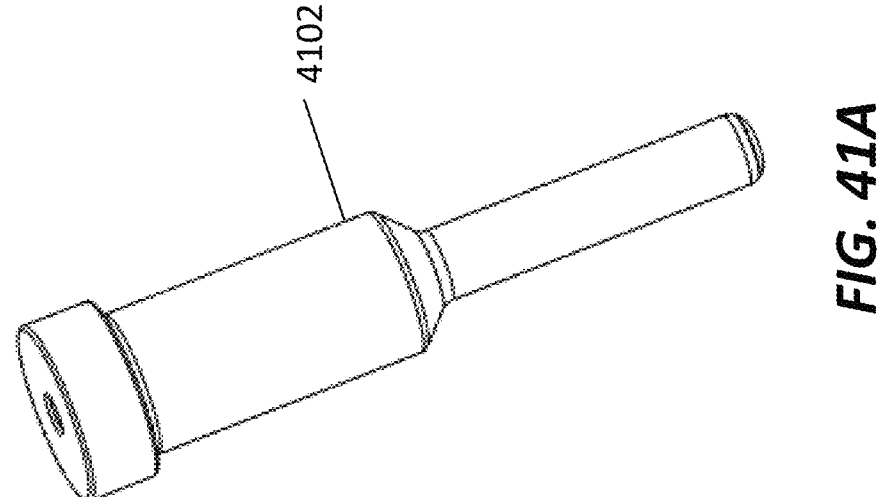
FIG. 41A illustrates an exemplary drill sleeve consistent with the principles of the present disclosure.

FIGS. 41A-B illustrate an exemplary drill sleeve 4102 (FIG. 41A) and drill bit 4104 (FIG. 41B) consistent with the principles of the present disclosure. Drill sleeve 4102 and drill bit 4104 may be used in conjunction with implants discussed above and a backpack 4202 as shown in FIG. 42.

Figure 42:
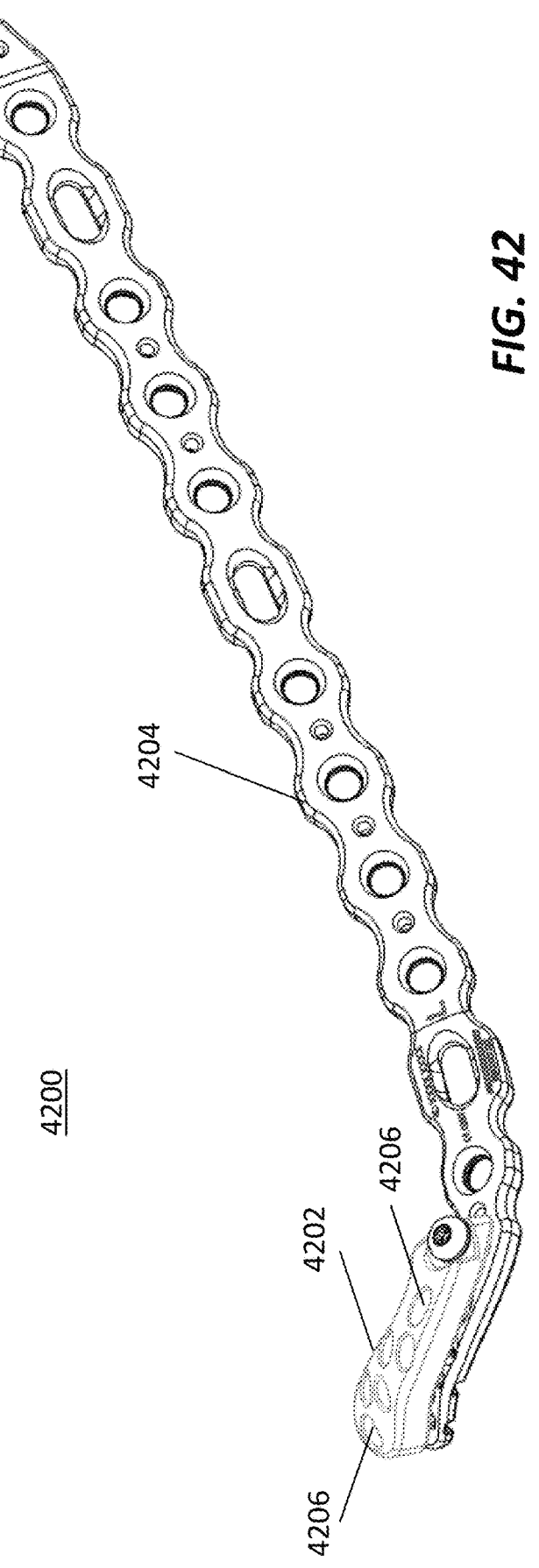
FIG. 42 illustrates an exemplary system for treating bone fractures consistent with the principles of the present disclosure, including a backpack and a bone plate.

FIG. 42 illustrates a system 4200 for treating bone fractures. System 4200 may comprise backpack 4202, implant or bone plate 4204, as well as bone screws described in detail above. Drill sleeve 4102 may be placed in proximity to the implant so that drill bit 4104 may be used to drill a hole in a bony structure that will ultimately be used to attach implant 4204 to the patient at the target area.

In order to provide a nominal trajectory for drill bit 4104, backpack 4202 may attach to implant 4204. Backpack 4202 may have holes 4206 that align with polyaxial holes of implant 4204. In order to secure backpack 4202 to implant 4204, a reverse collet mechanism may be used to engage and attach to implant 4204.

Figure 43:
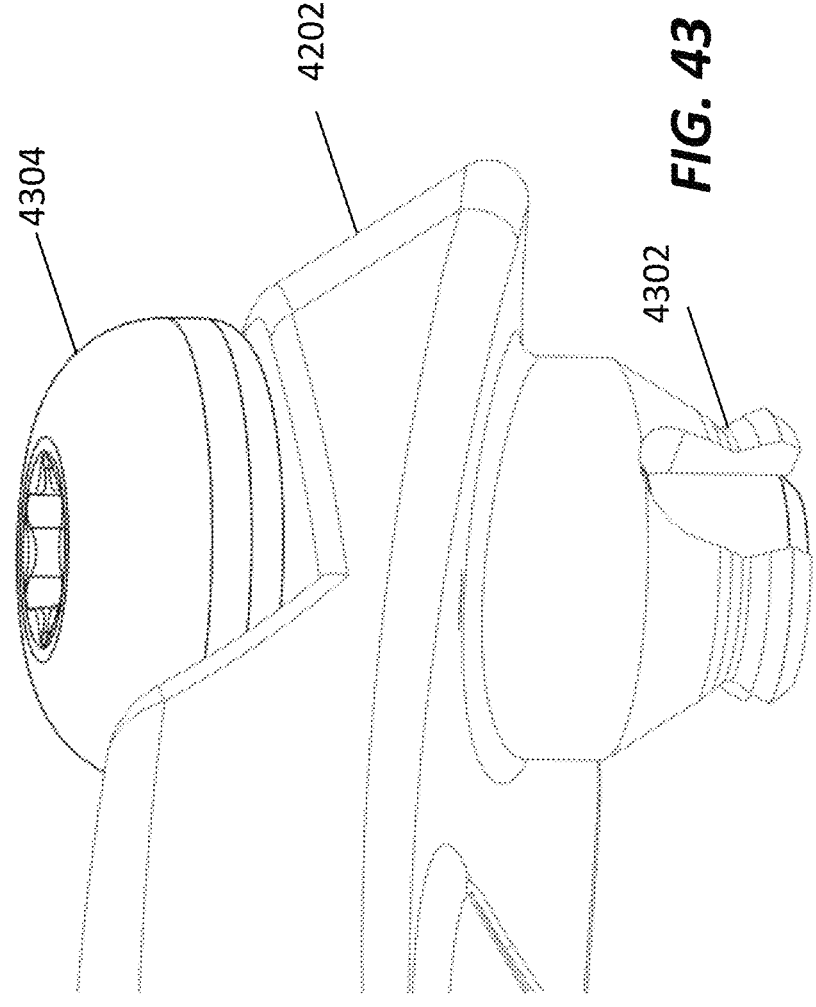
FIG. 43 illustrates and exemplary backpack consistent with the principles of the present disclosure.

FIG. 43 illustrates backpack 4202 in greater detail, including a reverse collet 4302 and a fastener 4304. Backpack 4204 may be inserted into implant 4204 in an unlocked position. Once inside a polyaxial hole of implant 4204, a user may tighten fastener 4304 into a locked position. In the locked position, backpack 4204 is rigidly engaged in the polyaxial hole of implant 4204. At this point, holes 4206 are aligned with polyaxial holes in implant 4204 in order to provide a nominal trajectory for a drill bit entering holes 4206 and ultimately into implant 4204 and the bone.

Figure 44:
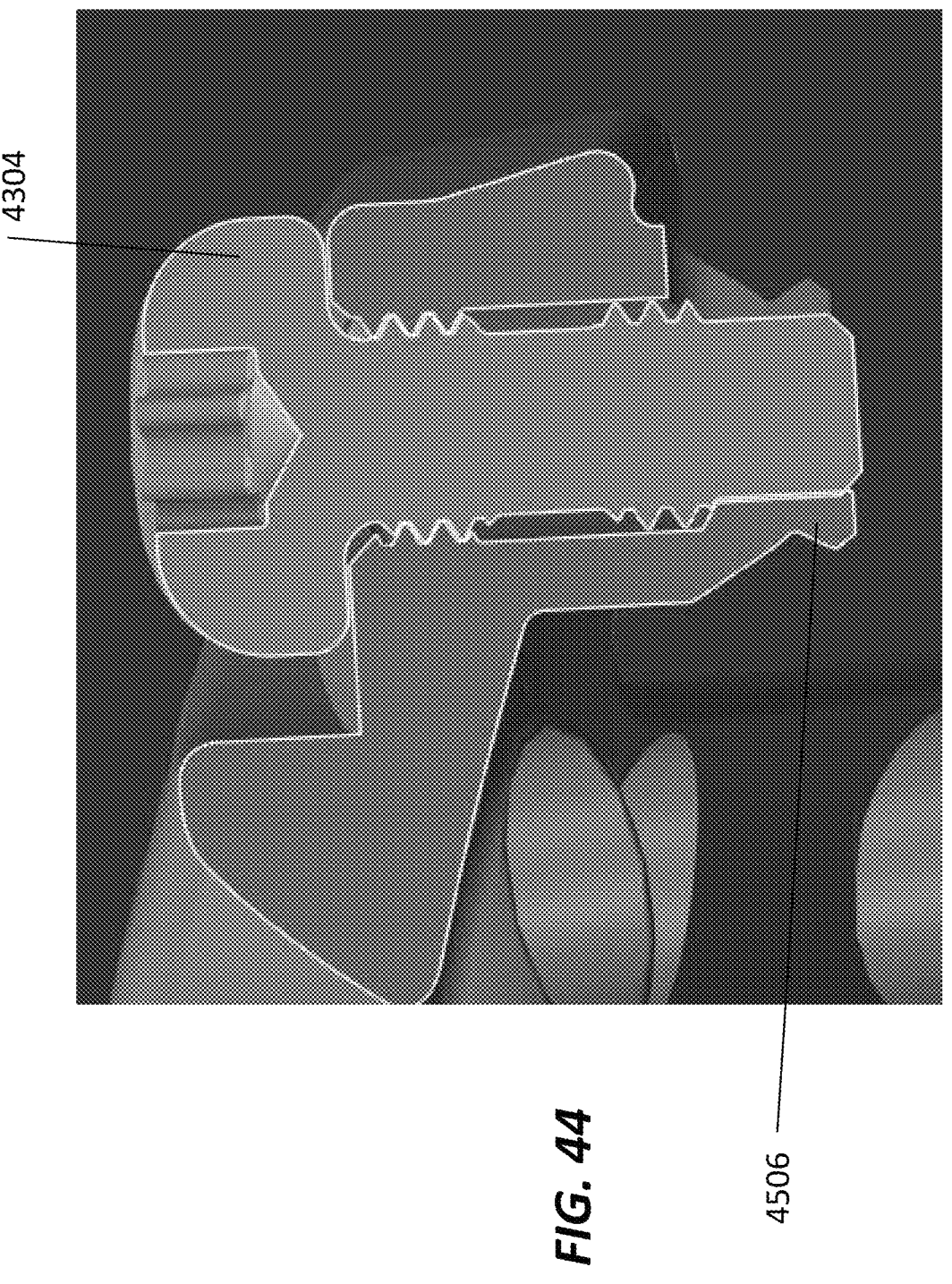
FIG. 44 illustrates an exemplary backpack attached to an implant consistent with the principles of the present disclosure.

FIG. 44 illustrates a cross-sectional view of fastener 4304 disposed within backpack 4202. After backpack 4202 is attached to implant 4204, system 4200 may be moved to a target bony area of a patient. A drill may be used to provide a trajectory through backpack 4202 and implant 4204 into a bone of patient. In this regard, backpack 4202 may provide a nominal trajectory into the bone for bone screws that attach implant 4204 to the target bony area. Once the trajectories are drilled into the bone, screws may be inserted through backpack 4202 to implant 4204 into the bone of the patient. Holes 4206 may be large enough to receive a screw and have the screw pass completely through hole 4206 to implant 4204. Once the user is finished inserting one or more bone screws to attach implant 4204, backpack 4204 may be unlocked and released from implant 4204 leaving just implant 4204 and screws attached to the bone.

Figures 45A, 45B:
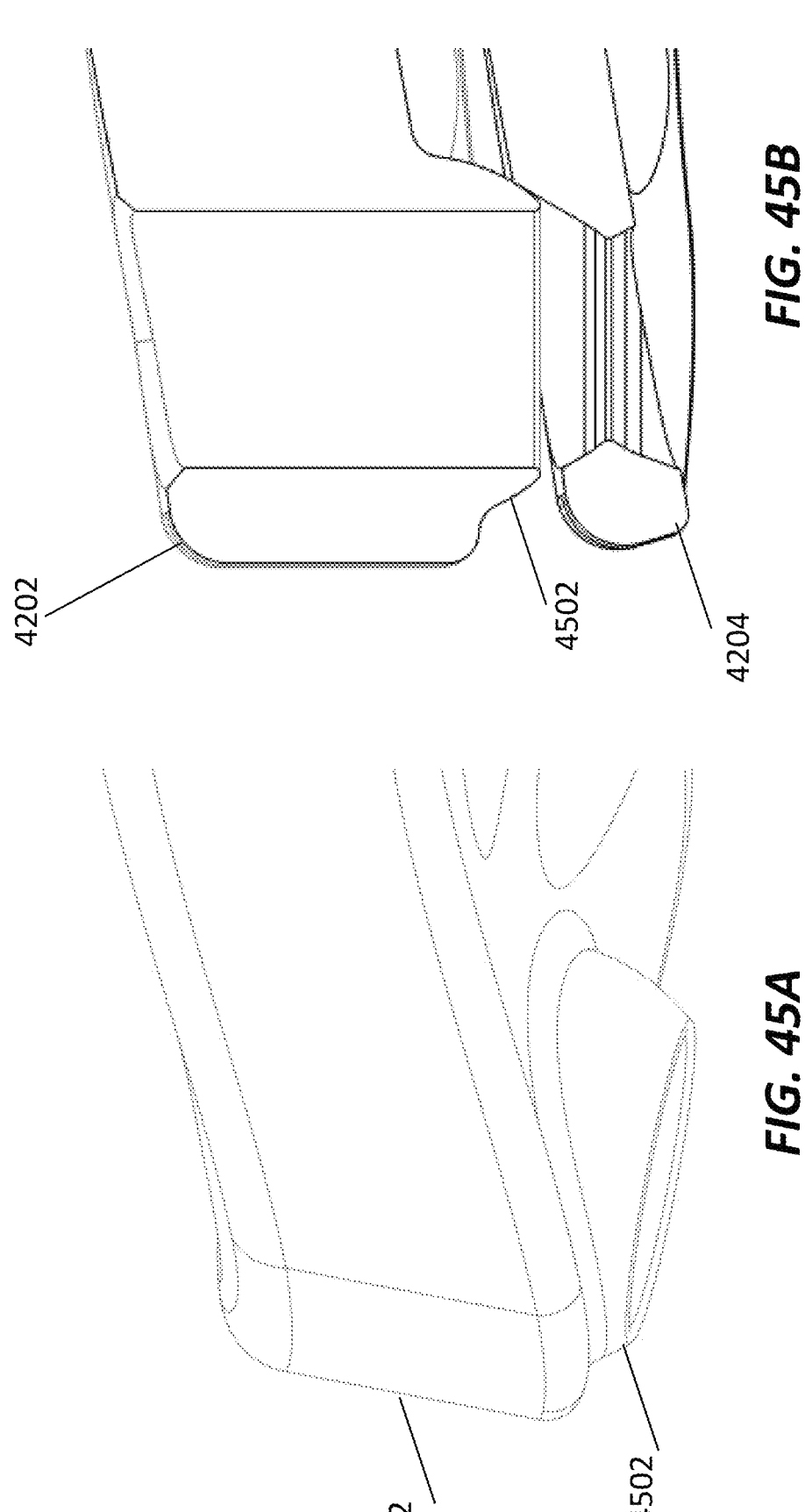
FIGS. 45A-45B illustrate an exemplary backpack consistent with the principles of the present disclosure.

FIGS. 45A-45B illustrate exemplary embodiments of backpack 4202 consistent with principles of the present disclosure. Backpack 4202 may comprise a standoff 4502 that may be configured to aid in lining up backpack 4202 with implant 4204. Standoff 4502 may be partially spherical or tapered in order to rest inside a hole in implant 4202 before fastener 4304 is disposed in backpack 4202 to attach implant 4204 to backpack 4202.

Figures 46A, 46B, 46C:
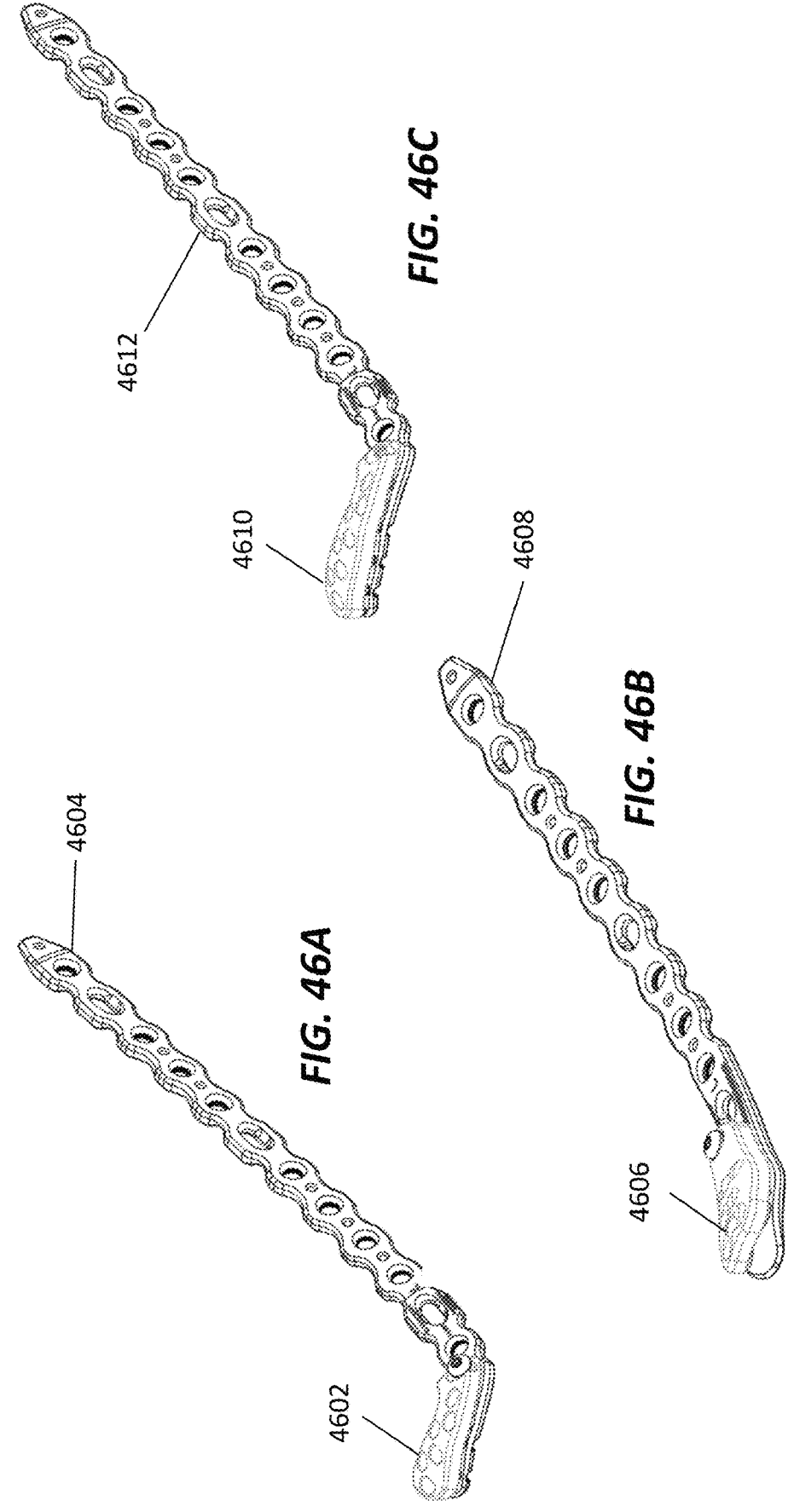
FIGS. 46A-46C illustrate exemplary systems for treating bone fractures consistent with the principles of the present disclosure.

FIGS. 46A-46C illustrate exemplary backpacks 4602, 4606, and 4610 and exemplary implants 4604, 4608, and 4612. For example, backpack 4602 may be configured to be used in with an anterolateral plate 4604, backpack 4606 may be configured to be used with a medial plate 4608, and backpack 4610 may be configured to be used with a wide anterolateral plate 4612.

One skilled in the art will appreciate that the embodiments discussed above are non-limiting. While bone plates may be described as suitable for a particular approach (e.g., medial or posterior), one skilled in the art will appreciate that the bone plates can be used for multiple approaches. In addition, while bone plates are described as having particular holes (e.g., locking or non-locking), one skilled in the art will appreciate that any of the bone plates can include locking, non-locking or a combination of locking and non-locking holes. In addition to the bone plates, screws and instruments described above, one skilled in the art will appreciate that these described features can be used with a number of trauma treatment instruments and implants, including fixators, rods, and other plates and screws.

Although the invention has been described in example embodiments, those skilled in the art will appreciate that various modifications may be made without departing from the spirit and scope of the invention. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto. The feature or features of one embodiment may be wholly or partially incorporated into another embodiment without departing from the scope of the invention.

What is claimed is:

1. A system for treating a fracture in a bone comprising:
a backpack having a plurality of backpack holes and a coupler hole including a reverse collet;
a bone plate configured to engage the bone and including:
a base extending along a first axis and having a plurality of base holes adapted to be aligned with corresponding backpack holes of the plurality of backpack holes, the plurality of base holes configured to receive bone fasteners, the base further having a coupler hole adapted to receive the reverse collet of the backpack; and
a shaft connected to the base and extending along a second axis different from the first axis, the shaft having a plurality of shaft holes for receiving bone fasteners, wherein the shaft includes a through hole between adjacent shaft holes of the plurality of shaft holes; and
a backpack fastener adapted to be inserted into the coupler hole of the backpack to selectively unlock and lock the reverse collet to the base,
wherein the coupler hole includes internal threading to threadingly receive the backpack fastener, and wherein the backpack fastener includes a shaft having first external threading and second external threading longitudinally spaced from the first external threading.

2. The system of claim 1, further comprising:
a drill bit; and
a drill sleeve configured to be placed in proximity to the bone plate and having a through hole for receiving the drill bit.

3. The system of claim 1, wherein at least one of the backpack holes includes an underside projection configured to rest in a corresponding base hole.

4. The system of claim 3, wherein the underside projection is a tapered projection that tapers in a downward direction.

5. The system of claim 1, wherein the base further comprises at least one suture hole adapted to receive a K-wire.

6. The system of claim 1, wherein one of the shaft holes is an elongated dynamic compression plating slot.

7. The system of claim 6, wherein the dynamic compression plating slot is at least twice a length of any of the other shaft holes.

8. The system of claim 1, wherein the shaft comprises at least four shaft holes including at least one compression slot.

* * * * *